United States Patent
Rosenberg et al.

(10) Patent No.: US 9,433,792 B2
(45) Date of Patent: Sep. 6, 2016

(54) SYSTEM AND METHOD FOR EVALUATING DIASTOLIC FUNCTION BASED ON CARDIOGENIC IMPEDANCE USING AN IMPLANTABLE MEDICAL DEVICE

(71) Applicant: PACESETTER, INC., Sylmar, CA (US)

(72) Inventors: Stuart Rosenberg, Castaic, CA (US); Kritika Gupta, San Francisco, CA (US); Riddhi Shah, San Jose, CA (US); Rupinder Bharmi, Canyon Country, CA (US); Edward Karst, Los Angeles, CA (US); Gene A. Bornzin, Simi Valley, CA (US)

(73) Assignee: PACESETTER, INC., Sylmar, CA (US)

(*) Notice: Subject to any disclaimer, the term of this patent is extended or adjusted under 35 U.S.C. 154(b) by 529 days.

(21) Appl. No.: 13/898,931

(22) Filed: May 21, 2013

(65) Prior Publication Data
US 2014/0350630 A1    Nov. 27, 2014

(51) Int. Cl.
| A61N 1/365 | (2006.01) |
|---|---|
| A61B 5/00 | (2006.01) |
| A61B 5/0295 | (2006.01) |
| A61B 5/053 | (2006.01) |
| A61N 1/368 | (2006.01) |

(52) U.S. Cl.
CPC ......... *A61N 1/36521* (2013.01); *A61B 5/0295* (2013.01); *A61B 5/0538* (2013.01); *A61B 5/7246* (2013.01); *A61N 1/3682* (2013.01); *A61N 1/3688* (2013.01)

(58) Field of Classification Search
USPC ........................................................ 600/509
See application file for complete search history.

(56) References Cited

U.S. PATENT DOCUMENTS

| 5,391,192 A * | 2/1995 | Lu ............................ A61N 1/37 600/510 |
|---|---|---|
| 5,601,613 A | 2/1997 | Florio et al. |
| 6,577,892 B2 | 6/2003 | Schomburg |
| 7,526,338 B1 | 4/2009 | Gill et al. |
| 7,662,086 B2 | 2/2010 | Bjorling |

(Continued)

OTHER PUBLICATIONS

Barold S. Serge et al, "Echocardiographic optimization of the atrioventricular and interventricular intervals during cardiac resynchronization," Europace 2008;10(suppl 3):iii88-ii95.

(Continued)

*Primary Examiner* — Christopher D Koharski
*Assistant Examiner* — Jeremiah Kimball

(57) ABSTRACT

Diastolic function is monitored within a patient based on dynamic cardiogenic impedance as measured by a pacemaker or other implantable medical device. In one example, the device uses ventricular cardiogenic impedance values to detect E-wave parameters representative of passive filling of the ventricles. Atrial cardiogenic impedance values are used to detect A-wave parameters representative of active filling of the ventricles. Diastolic function is then assessed or evaluated based on the E-wave and A-wave parameters. Various functions of the implantable device are then controlled based on the assessment of diastolic function, such as by adjusting atrioventricular delay parameters to improve diastolic function. In some examples, the detection of E- and A-wave parameters is achieved by aligning impedance signals to atrial activation, and separately to ventricular activation, during asynchronous VOO pacing or while artificially inducing a 2:1 block.

26 Claims, 12 Drawing Sheets

(56) References Cited

U.S. PATENT DOCUMENTS

| | | | |
|---|---|---|---|
| 7,751,888 B1 * | 7/2010 | Schecter | A61N 1/3627 607/17 |
| 7,850,616 B1 | 12/2010 | Gill et al. | |
| 7,959,576 B2 | 6/2011 | Torpo et al. | |
| 8,280,523 B2 | 10/2012 | Keel et al. | |
| 8,285,377 B2 | 10/2012 | Rosenberg et al. | |
| 8,326,419 B2 | 12/2012 | Rosenberg et al. | |
| 8,412,327 B2 | 4/2013 | Hou et al. | |
| 8,702,616 B2 | 4/2014 | Gill et al. | |
| 2001/0021814 A1 | 9/2001 | Schomburg | |
| 2003/0009197 A1 * | 1/2003 | Helland | A61N 1/368 607/9 |
| 2005/0182447 A1 * | 8/2005 | Schecter | A61N 1/3627 607/2 |
| 2007/0191901 A1 * | 8/2007 | Schecter | A61N 1/3627 607/17 |
| 2009/0281440 A1 * | 11/2009 | Farazi | A61B 5/02405 600/510 |
| 2011/0009754 A1 * | 1/2011 | Wenzel | A61B 5/0215 600/485 |
| 2011/0054560 A1 | 3/2011 | Rosenberg et al. | |
| 2011/0160787 A1 * | 6/2011 | Greenhut | A61N 1/36564 607/17 |
| 2011/0230746 A1 | 9/2011 | Jarverud et al. | |
| 2011/0319954 A1 | 12/2011 | Niazi et al. | |
| 2012/0109245 A1 | 5/2012 | Hettrick et al. | |

OTHER PUBLICATIONS

Extended EP Search Report, dated Sep. 26, 2014, EP Counterpart: App No. 14159946.4.

* cited by examiner

FIG. 6 — E-WAVE TEMPLATE GENERATION AND PROCESSING

300 — DURING SETUP, GENERATE ONE OR MORE E-WAVE TEMPLATES REPRESENTING PASSIVE FILLING OF THE VENT. BASED ON VENT. $Z_c$ VALUES BY:

- MEASURING VENT. $Z_c$ VALUES DURING A PERIOD OF NON-DEMAND PACING OVER A SET OF CARDIAC CYCLES (E.G. 30 SECS); OR DURING VENT. PACING DURING AF OR DURING AMS;

- DETECTING VENT. ACTIVATION EVENTS (V-PULSE/V-SENSE) WITHIN THE CARDIAC CYCLES (WITH SUITABLE BLANKING);

- ALIGNING THE MEASURED VENT. $Z_c$ VALUES TO DETECTED VENT. ACTIVATION EVENTS OF CORRESPONDING CYCLES SUCH THAT A-PACE/A-SENSE EVENTS ARE APPROXIMATELY UNIFORMLY DISTRIBUTED SO THE CONTRIBUTION FROM ACTIVE ATRIAL FILLING SUMS TO A SUBSTANTIALLY NEGLIGIBLE LEVEL;

- ENSEMBLE AVERAGING THE ALIGNED VENT. $Z_c$ VALUES (INCLUDING A DURATION OF 1.5 TO 2 CARDIAC CYCLES);

- DETECTING T-WAVES WITHIN CORRES. CARDIAC CYCLES;

- IDENTIFYING A SEGMENT OF DECREASING $Z_c$ WITHIN THE ENSEMBLE AVERAGED VENT. $Z_c$ VALUES FOLLOWING CORRESPONDING T-WAVES WITHIN THE CARDIAC CYCLES (SUCH AS FROM THE BEGINNING OF THE DOWNSTROKE OF $Z_c$ DURING DIASTOLE UNTIL BEGINNING OF THE UPSTROKE SHORTLY AFTER VENT. ACTIVATION); AND

- STORING THE SEGMENT OF DECREASING $Z_c$ AS AN E-WAVE TEMPLATE (THEN INTERMITTENTLY VARYING AV DELAYS FOR A FEW BEATS AND REPEATING THE PROCEDURE TO GENERATE ADDITIONAL TEMPLATES FOR DIFFERENT AV DELAY VALUES)

302 — IN USE, MEASURE ADDITIONAL VENT. $Z_c$ VALUES (REPRESENTATIVE OF PASSIVE FILLING) DURING NEWLY-DETECTED CARDIAC CYCLES

304 — DETERMINE CONVOLUTION/CROSS-CORRELATION OF THE E-WAVE TEMPLATE WITH THE ADDITIONAL VENT. $Z_c$ VALUES TO DERIVE E-WAVE PARAMS. REPRESENTATIVE OF PASSIVE FILLING CONTRIBUTIONS TO DIAST. FUNCTION WITHIN THE NEWLY-DETECTED CARDIAC CYCLES (WITH THE TIME/PHASE SHIFT RESULTING IN GREATEST CORRELATION COEF. INDICATING E-WAVE TIMING AND DEGREE/VALUE OF PEAK CORREL. PROVIDING A RELATIVE METRIC OF THE STRENGTH OF E-WAVE) AND/OR BASED ON A METRIC VALUE OBTAINED BY CALCULATING THE INTEGRAL OF VENT. $Z_c$ VALUES OF THE SUBS. CARDIAC CYCLE FOR SAMPLES WHERE A CORRELATION COEF. BETWEEN THE E-WAVE TEMPLATE AND THE VENT. $Z_c$ VALUES OF THE SUBSEQUENT CYCLE EXCEEDS A PREDETERMINED THRESHOLD

FIG. 7

( A-WAVE TEMPLATE GENERATION AND PROCESSING )

DURING SETUP, GENERATE ONE OR MORE A-WAVE IMPEDANCE TEMPLATES REPRESENTATIVE OF ACTIVE FILLING OF THE VENTRICLES BASED ON ATRIAL Zc VALUES BY:

MEASURING ATRIAL Zc VALUES DURING A PERIOD OF NON-DEMAND PACING OVER A SET OF CARDIAC CYCLES (E.G. 30 SECS);

DETECTING ATRIAL ACTIVATION EVENTS (A-PULSE/A-SENSE) WITHIN THE CARDIAC CYCLES (WITH SUITABLE BLANKING);

ALIGNING THE MEASURED ATRIAL Zc VALUES TO DETECTED ATRIAL ACTIVATION EVENTS OF CORRESPONDING CYCLES SUCH THAT V-PACE/V-SENSE EVENTS ARE APPROXIMATELY UNIFORMLY DISTRIBUTED SO THE CONTRIBUTION FROM VENT. ACTIVATION AND RELAXATION (I.E. THE E-WAVE) SUMS TO A SUBSTANTIALLY NEGLIGIBLE LEVEL;

ENSEMBLE AVERAGING THE ALIGNED ATRIAL Zc VALUES (INCLUDING A DURATION OF 1 TO 1.5 CARDIAC CYCLES);

IDENTIFYING A SEGMENT OF INCREASING Zc WITHIN THE ENSEMBLE AVERAGED ATRIAL Zc VALUES FOLLOWING CORRESPONDING A-PULSE/A-SENSE WITHIN THE CARDIAC CYCLES (SUCH AS FROM THE BEGINNING OF THE UPSTROKE OF Zc DURING ATRIAL SYSTOLE UNTIL THE SUBSEQUENT FLAT OR DOWNSTROKE PORTION); AND

STORING THE SEGMENT OF DECREASING Zc AS AN A-WAVE TEMPLATE (THEN INTERMITTENTLY VARYING AV DELAYS FOR A FEW BEATS AND REPEATING THE PROCEDURE TO GENERATE ADDITIONAL TEMPLATES FOR DIFFERENT AV DELAY VALUES)

— 350

IN USE, MEASURE ADDITIONAL ATRIAL Zc VALUES (REPRESENTATIVE OF ACTIVE FILLING OF VENT.) DURING NEWLY-DETECTED CARDIAC CYCLES

— 352

DETERMINE CROSS-CORRELATION/CONVOLUTION OF THE A-WAVE TEMPLATE WITH THE ADDITIONAL ATRIAL Zc VALUES TO DERIVE A-WAVE PARAMS. REPRESENTATIVE OF ACTIVE FILLING CONTRIBUTIONS TO DIAST. FUNCTION WITHIN THE NEWLY-DETECTED CARDIAC CYCLES (WITH THE TIME/PHASE SHIFT RESULTING IN GREATEST CORRELATION COEF. INDICATING A-WAVE TIMING AND DEGREE/VALUE OF PEAK CORREL. PROVIDING A RELATIVE METRIC OF THE STRENGTH OF A-WAVE) AND/OR BASED ON A METRIC VALUE OBTAINED BY CALCULATING THE INTEGRAL OF ATRIAL Zc VALUES OF THE SUBS. CARDIAC CYCLE FOR SAMPLES WHERE A CORRELATION COEF. BETWEEN THE A-WAVE TEMPLATE AND THE ATRIAL Zc VALUES OF THE SUBSEQUENT CYCLE EXCEEDS A PREDETERMINED THRESHOLD

— 354

SYSTEM AND METHOD FOR EVALUATING
DIASTOLIC FUNCTION BASED ON
CARDIOGENIC IMPEDANCE USING AN
IMPLANTABLE MEDICAL DEVICE

FIELD OF THE INVENTION

The invention generally relates to implantable medical devices, such as pacemakers or cardiac resynchronization therapy (CRT) devices, and in particular to techniques for evaluating or monitoring diastolic function within patients in which such devices are implanted.

BACKGROUND OF THE INVENTION

Heart failure is a debilitating disease in which progressive decrease in function of the heart results in inadequate blood flow to the tissues and organs of the body. The heart may lose propulsive power because of a decrease in ability of the cardiac muscle to contract, impaired filling of the chambers of the heart or both. Often, it is the ventricles that do not adequately eject or fill with blood over the cardiac cycle, and the valves regulating blood flow become leaky, allowing regurgitation or back-flow of blood. The impairment of arterial blood flow deprives the body's organs of oxygen and nutrients. Additionally, a cascade of maladaptive neurohormonal responses may take place, bringing about fluid and sodium retention, autonomic imbalance, vascular and cardiac remodeling and possibly dilatation of the heart. Fatigue, weakness and the inability to carry out daily tasks may result. Not all heart failure patients suffer debilitating symptoms immediately. Some may live actively for years. Yet, with few exceptions, the disease is relentlessly progressive.

Nearly half of those with heart failure suffer from diastolic dysfunction, also called diastolic heart failure (DHF) or heart failure with preserved ejection fraction (HFpEF), wherein systolic function is generally preserved but diastolic function is compromised. Diastolic dysfunction refers to an abnormality in the ability of the heart to fill during diastole, which is the phase of the cardiac cycle when the ventricles relax and fill with blood prior to contraction. With DHF, an assessment of ventricular filling is particularly important for managing patients. There may be impaired diastolic function in many patients with systolic heart failure as well, which may help to understand the variable response of these patients to therapies aimed to treat systolic dysfunction. Currently, noninvasive assessment of diastolic function is typically done using echocardiography by detecting and examining E-waves and A-waves in conjunction with an electrocardiogram (ECG.) The E-wave corresponds to the flow of blood across the mitral valve during early diastole; the A-wave corresponds to flow of blood across the mitral valve during atrial contraction near the end of ventricular diastole. See, for example, Barold et al, Europace 2008; 10 (suppl 3):iii88.

Echocardiographic assessment of ventricular filling in diastole is useful both for diagnostic purposes as well as for guiding programming of cardiac devices. However, echocardiography can be time consuming and operator dependent, and is not often used in clinical practice. In fact, there is a lack of evidence suggesting beneficial impact of biventricular pacing devices in patients with primarily diastolic dysfunction. The utility of a device might be increased if it could be used to optimize diastolic function. Thus, techniques for more easily and reliably assessing ventricular filling would be valuable for both in-clinic and ambulatory adjustment of pacing control parameters (such as atrioventricular delay (AVD) parameters) within pacemakers, CRTs or other cardiac rhythm management devices (CRMDs), as well as for early detection of changes in the cardiac condition. It is to these ends that the invention is generally directed. In particular, systems and methods are provided for use with CRMDs to exploit dynamic cardiogenic impedance (i.e. Zc) signals to estimate diastolic function, specifically diastolic flow characterization of passive early filling (equivalent to the echocardiographic E-wave) and atrial kick (equivalent to the echocardiographic A-wave.)

SUMMARY OF THE INVENTION

In accordance with exemplary embodiments of the invention, techniques are provided for assessing, monitoring or evaluating diastolic function within a patient using an implantable medical device such as a pacemaker, CRT or other CRMD. Briefly, values representative of ventricular cardiogenic impedance are measured by the device, and E-wave parameters representative of passive filling of the ventricles are derived therefrom. Values representative of atrial cardiogenic impedance are also measured, and A-wave parameters representative of active filling of the ventricles are derived therefrom. Diastolic function is assessed or evaluated based on the E-wave and A-wave parameters. One or more functions of the implantable device are then controlled based on the assessment of diastolic function, such as by adjusting AVD parameters to preferred or optimal values, or otherwise titrating the delivery of therapy in response to diastolic dysfunction. In at least some examples, the foregoing is achieved by aligning impedance waveforms to atrial activation, and separately to ventricular activation, during asynchronous VOO pacing (or other forms of "non-demand" pacing such as DOO.)

In an illustrative example of the invention, ventricular cardiogenic impedance values are measured along a vector between a right ventricular (RV) coil electrode and a housing of the device. An E-wave impedance template representative of passive filling of the ventricles is initially generated for the patient based on ventricular impedance values measured during a period of non-demand pacing. This may be performed, for example, during an initial setup procedure. Thereafter, additional ventricular impedance values are measured during a subsequent cardiac cycle to be examined. A convolution of the E-wave impedance template with the additional ventricular impedance values is performed (such as by calculating the cross-correlation) so as to derive E-wave parameters representative of passive filling contributions to diastolic function within the particular cardiac cycle being examined. Specific E-wave parameters derived using this procedure may include the timing of the E-wave within the particular cardiac cycle, as well as the amount of blood received by the ventricles during the cardiac cycle due to passive filling.

In the illustrative example, the E-wave template is initially generated by: measuring ventricular cardiogenic impedance values during the initial period of non-demand pacing (such as VOO pacing or DOO pacing with selected AVD); detecting ventricular activation events (R-waves) within a corresponding intracardiac electrogram (IEGM); aligning the measured ventricular cardiogenic impedance waveform to the detected ventricular activation events; ensemble averaging the aligned ventricular cardiogenic impedance values; detecting corresponding ventricular repolarization events (T-waves) within the cardiac cycles; identifying a segment of decreasing impedance within the ensemble averaged ventricular cardiogenic impedance values following corresponding ventricular repolarization events within the cardiac cycles; and then storing the segment of decreasing impedance as the E-wave template. Note that the ensemble average of RV coil-case impedance waveform (aligned by ventricular activation) will have approximately uniformly distributed P-waves, so the contribution from active atrial filling (the A-wave) sums to a substantially negligible level. However, early diastolic filling (the E-wave) occurs a fixed time after ventricular activation, and is thereby reflected in the diastolic period averaged RV coil-case cardiogenic impedance.

Still further, in the illustrative example, the atrial cardiogenic impedance values are measured along a vector between a right atrial (RA) electrode and a housing of the device. An A-wave impedance template representative of active filling of the ventricles is also generated based on atrial cardiogenic impedance values measured during an initial period of non-demand pacing (such as during a setup procedure.) Thereafter, additional atrial impedance values are measured during the subsequent cardiac cycle to be examined. A convolution of the A-wave impedance template with the additional atrial impedance values is performed so as to derive A-wave parameters representative of active filling contributions to diastolic function within the particular cardiac cycle being examined. Specific A-wave parameters derived may include the timing of the A-wave of the particular cardiac cycle, as well as the amount of blood received by the ventricles during that cardiac cycle due to active filling.

In the illustrative example, the A-wave template is initially generated by: measuring atrial cardiogenic impedance values during the initial period of non-demand pacing; detecting atrial activation events (P-waves) within the cardiac cycles; aligning the measured atrial cardiogenic impedance waveforms to the detected atrial activation events of corresponding cardiac cycles; ensemble averaging the aligned atrial cardiogenic impedance values; identifying a segment of increasing impedance within the ensemble averaged atrial cardiogenic impedance values following corresponding atrial activation events within the cardiac cycles; and then storing the segment of increasing impedance as the A-wave template representative of active filling contributions to diastolic function. Note that the ensemble average of RA-case impedance beats (aligned by atrial activation) will have approximately uniformly distributed ventricular pacing, so any contribution from ventricular activation or relaxation (the E-wave) will sum to a substantially negligible level. However, active atrial filling of the ventricles (the A-wave) occurs a fixed time after atrial electrical activation, and is thereby reflected in the averaged RA-case dynamic impedance.

Further with regard to the generation of the E-wave and A-wave templates, the initial period of non-demand pacing used to generate the templates may include pacing at a rate sufficient to trigger an artificial 2:1 block to emphasize the active and passive filling contributions to diastolic function. Thereafter, diastolic function may be assessed or evaluated based on the newly-detected E-wave and A-wave parameters by tracking passive filling contributions to diastolic function based on the E-wave parameters and tracking active filling contributions to diastolic function based on the A-wave parameters. The AVD (or other suitable pacing parameters) may be controlled or adjusted based on the E-wave and A-wave waveforms to, for example, avoid fusion of the A-wave and E-wave and/or avoid truncation of the A-wave, or otherwise address any other aspects of diastolic dysfunction. Still further, the period of non-demand pacing can include ventricular pacing during atrial fibrillation or during automatic mode switch (at least insofar as E-waves are concerned.)

Additionally or alternatively, AV pacing delays may be intermittently varied from a currently-programmed setting to a different setting for a few beats to generate the aforementioned impedance templates for different AV delay values. Such varying can take place over the course of a day or night and over several days or weeks, and the AV delays can range from very short to very long. In this manner, templates may be generated using all of the varying AV delays acquired over time, rather than collecting data in VOO mode only for the template generation. Once templates have been acquired for E- and A-waves, the individual beats making up the templates for each particular AV delay are analyzed by the implanted device (or an external system) to determine relative filling contributions so as to make AVD recommendations, etc.

In yet another embodiment of the invention, rather than assessing only the E-wave contributions from the RV-case vector, the net ventricular filling of combined E- and A-waves are extracted from the morphology of RV-case vector. For example, ventricular cardiogenic impedance values are measured and combined A-wave and E-wave parameters representative of both passive and active filling of the ventricles of are derived from the ventricular cardiogenic impedance values. Atrial cardiogenic impedance values are also measured and A-wave parameters representative of active filling of the ventricles are derived therefrom. Diastolic function is then assessed or evaluated based on the combined A-wave and E-wave parameters derived from the ventricular cardiogenic impedance values and the separate A-wave parameters derived from the atrial cardiogenic impedance values. One or more functions of the implantable device are then controlled based on the assessment of diastolic function, such as adjusting AVD parameters, detecting and tracking diastolic dysfunction, etc.

In some implementations, the implanted device itself performs the foregoing functions and procedures. In other examples, an external device such as a programmer performs all or some of the functions and procedures based on impedance data sent to it by the implanted device under the supervision of a clinician. Moreover, whereas the examples described herein primarily exploit impedance, other related electrical parameters may be used, where appropriate, such as admittance, conductance or immittance. Hence, "values representative of impedance" can include, e.g. impedance, admittance, conductance and/or immittance. System and method examples of the invention are described herein below.

BRIEF DESCRIPTION OF THE DRAWINGS

The above and further features, advantages and benefits of the invention will be apparent upon consideration of the present description taken in conjunction with the accompanying drawings, in which:

FIG. 6 illustrates and highlights certain aspects of the procedure of FIG. 4, particularly the generation and exploitation of the E-wave template;

FIG. 7 illustrates and highlights certain aspects of the procedure of FIG. 4, particularly the generation and exploitation to the A-wave template;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
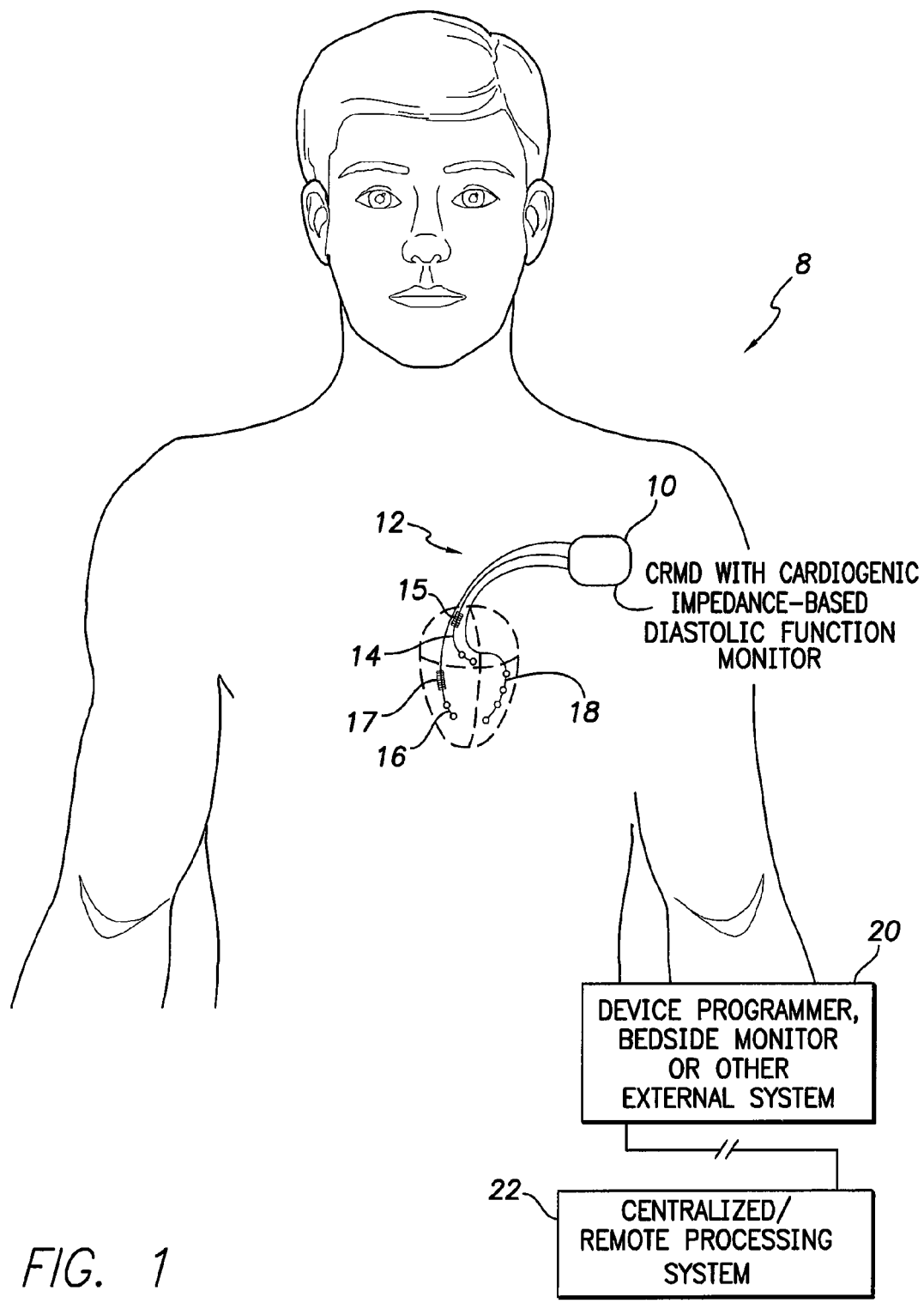
FIG. 1 illustrates pertinent components of an implantable medical system having a pacemaker, CRT or other suitable device equipped to assess or monitor diastolic function based on cardiogenic impedance (alone or in conjunction with an external system)

FIG. 1 illustrates an implantable medical system 8 capable of assessing, monitoring and/or evaluating diastolic function based on cardiogenic impedance within the patient. To this end, medical system 8 includes a CRMD 10—such as a pacemaker, CRT device, diastolic function monitor, or implantable cardioverter-defibrillator (ICD)—capable of delivering electrical pulses via a set of cardiac leads 12 implanted on or within the heart of the patient and further capable of measuring, sensing or detecting dynamic cardiogenic impedance values or parameters in response thereto. Three exemplary leads are shown in stylized form: an RA lead 14, an RV lead 16 and a left ventricular (LV) lead 18 implanted via the coronary sinus (CS). Some exemplary electrodes are also shown, including an RA coil electrode 15 and an RV coil electrode 17, which are used in some examples to measure impedance in conjunction with the housing of the CRMD device. A more complete illustration of an exemplary set of leads is provided in FIG. 10. In use, morphological features of the cardiogenic impedance signals corresponding to E-waves and A-waves are detected and examined to assess diastolic function and to set the AVD (or other pacing control parameters) to optimal or preferred values. Diastolic function can also be tracked over time to detect and monitor diastolic dysfunction (such as DHF) and to track progression of diastolic dysfunction. Warning signals may be generated (when appropriate) using an internal warning device within CRMD 10 or using an external device 20 (such as a bedside monitor or device programmer.)

External device 20 may be networked with an internet network site or other centralized/remote processing system 22 for relaying information to a clinician pertaining to diastolic dysfunction or other issues. The centralized system may include such systems as Merlin.Net™ of St. Jude Medical, which may be used in conjunction with bedside monitors or similar devices such as the HouseCall™ remote monitoring system or the Merlin@home™ systems, also of St. Jude Medical. Depending upon the implementation, the CRMD analyzes the cardiogenic impedance to assess diastolic function, set the AVD to optimal values, etc. In other implementations, the CRMD transmits its impedance measurements to external system 20, which performs the analysis or relays the data to remote system 22 for analysis, with the clinician then reprogramming AVD values (if needed) using a device programmer. The clinician may also prescribe any other appropriate therapies to address diastolic dysfunction or other issues. The clinician may also adjust the operation of the CRMD to activate, deactivate or otherwise control any other therapies that are automatically applied, such as CRT. Additionally, depending upon its capabilities, the CRMD also performs a wide variety of pacing and defibrillation functions, such as delivering pacing in response to arrhythmias or generating and delivering high-voltage shocks in response to ventricular fibrillation.

Note that embodiments may be implemented that do not perform all of these functions. Moreover, systems provided in accordance with the invention need not include all of the components shown in FIG. 1 or in the other figures described herein. No attempt is made herein to describe all possible combinations of components that may be provided in accordance with the general principles of the invention. Also, note that, the particular shape, size and locations of the implanted components are merely illustrative and may not necessarily correspond to actual implant locations.

Overview of Impedance-Based Diastolic Function Assessment Techniques

Figure 2:
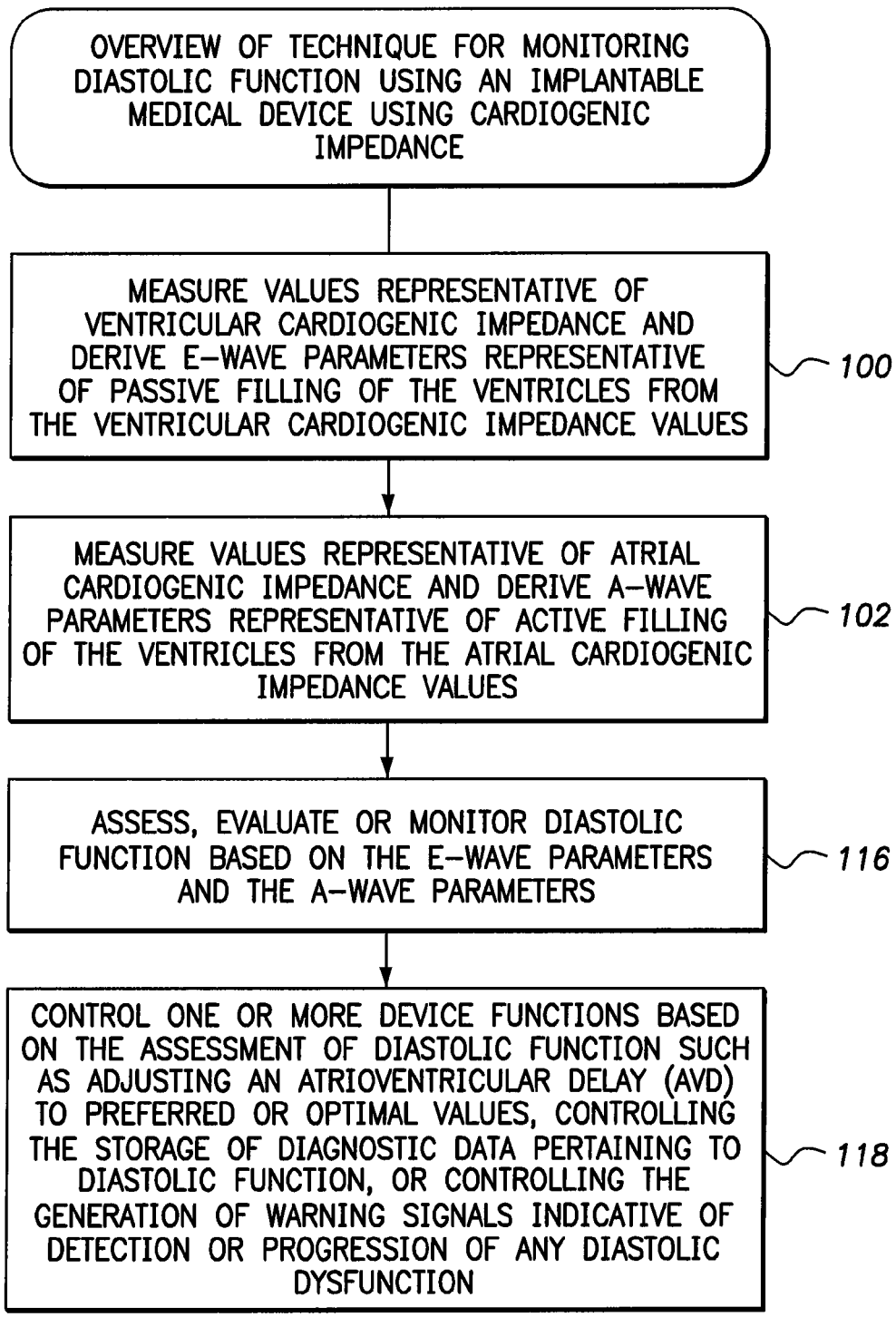
FIG. 2 is a flowchart providing an overview of a diastolic function assessment technique performed by the system of FIG. 1.
Figure 3:
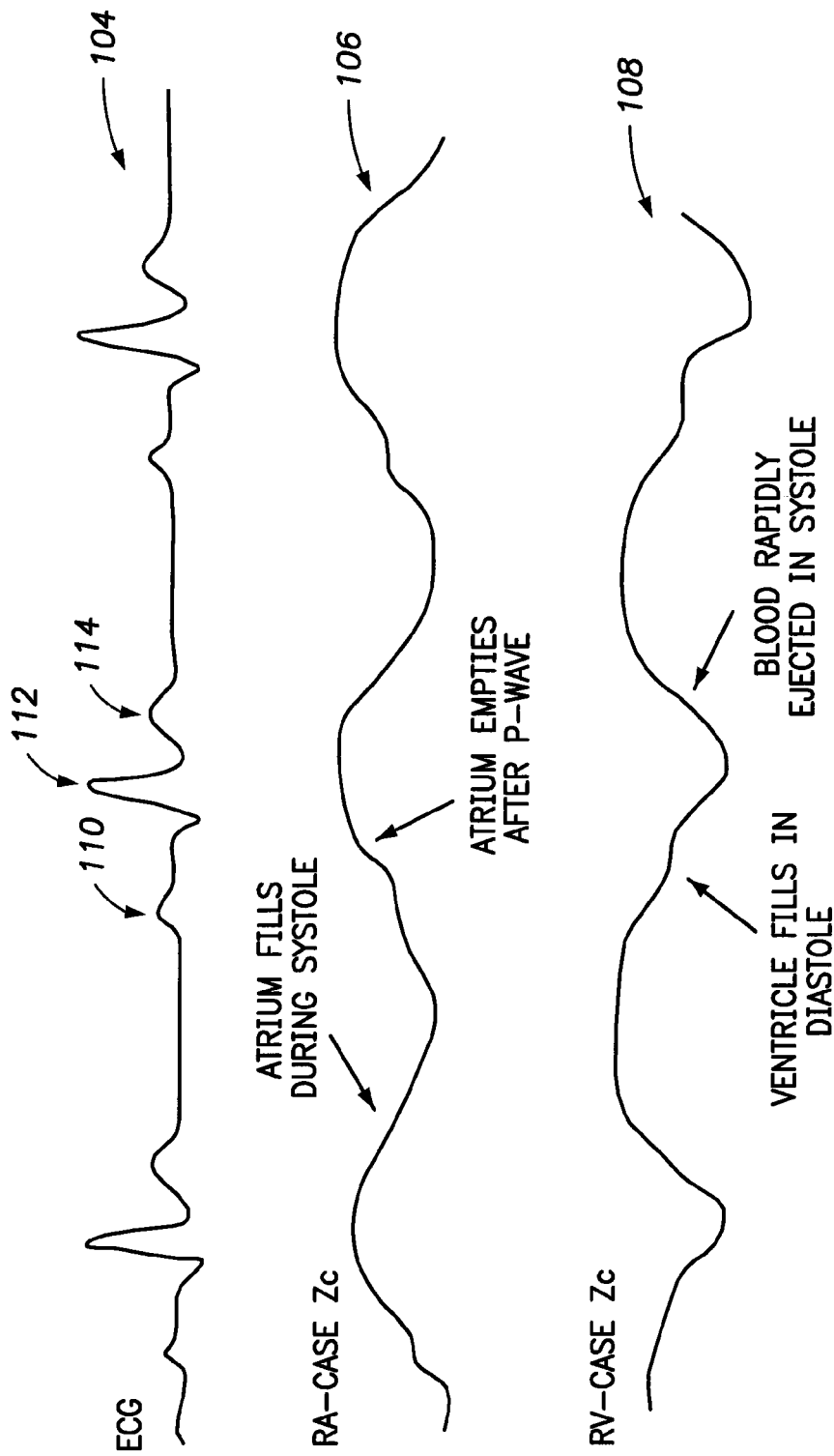
FIG. 3 is a graph illustrating particular cardiogenic impedance signals exploited by the technique of FIG. 3.

FIGS. 2 and 3 summarize a general technique for assessing or monitoring diastolic function based on cardiogenic impedance employed by the system of FIG. 1 or other suitably equipped systems. Beginning at step 100, the implanted device, measures values representative of ventricular cardiogenic impedance and derives E-wave parameters representative of passive filling of the ventricles from the ventricular cardiogenic impedance values. Ventricular cardiogenic impedance may be measured, for example, along a vector between the RV coil electrode and the device case or housing (also referred to as the "can".) At step 102, the device also measures values representative of atrial cardiogenic impedance and derives A-wave parameters representative of active filling of the ventricles from the atrial cardiogenic impedance values. Atrial cardiogenic impedance may be measured, for example, along a vector between an RA electrode and the device case. Note that, although steps 100 and 102 are shown sequentially, these steps may be performed concurrently (subject to the capabilities of the device itself) or in the opposite order.

Otherwise conventional impedance measurement techniques can be employed to detect the values representative of impedance. However, a particularly effective tri-phasic impedance detection pulse for use in measuring impedance is described in U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." See, also, techniques described in U.S. Published Application 2012/0035495 of Gutfinger et al., entitled "Systems and Methods for Exploiting Near-Field Impedance and Admittance for use with Implantable Medical Devices" and U.S. Published Application 2012/0035493 of Gutfinger et al., entitled "Near Field-Based Systems and Methods for Assessing Impedance and Admittance for use with an Implantable Medical Device."

Insofar as deriving cardiogenic (i.e. Zc) components of the impedance signals is concerned, predetermined "Zc" filter settings may be applied (i.e. a passband allowing cardiogenic dynamic content to pass while largely rejecting respiratory and static/thoracic fluid effects) to different device-based impedance vectors, with the resulting impedance traces having specific meanings. In particular, an RA-case impedance vector has been found to correspond primarily to atrial volume. Current is generated between the RA ring and case electrodes; voltage is measured between RA tip and case (i.e. the RA-case vector.) It is believed that upward deflections in the RA-case impedance vector waveform correspond to atrial emptying into the ventricle and downward deflections correspond to atrial filling from venous return. To assess ventricular volume, an RV-case vector may be used. Current is generated between the RV coil and case electrodes; voltage is measured between RV coil and case (i.e. the RV coil-case vector). It is believed that upward deflections in the RV-case impedance vector waveform correspond to ventricular ejection and downward deflections correspond to ventricular filling. As noted, other related electrical parameters besides impedance might be used, where appropriate, such as admittance, conductance or immittance.

Those skilled in the art can convert between these related parameters as needed and where appropriate. In some instances, the real component of impedance (i.e. resistance) might be exploited. Also, other vectors can be used, where appropriate. For example, the atrial vector could be from RA to a proximal electrode on multipolar LV lead, or from proximal electrode of LV lead to case. The ventricular vector could be from and RV lead electrode to an LV lead electrode, or from LV electrode to case.

Exemplary atrial and ventricular cardiogenic impedance waveforms are shown in FIG. 3 along with a corresponding surface ECG (provided to show the relative timing of events with the ECG and the impedance signals.) More specifically, FIG. 3 illustrates an ECG trace 104, an RA-case cardiogenic impedance trace 106 and RV-case cardiogenic impedance trace 108. Each trace covers about three heart beats. Within the ECG, individual cardiac electrical events are visible, including the P-wave 110, R-wave 112 (or QRS-complex) and the T-wave 114. Within the RA-case impedance trace, the period of time during which the atria fill with blood during systole is specifically indicated, as well as the period of time during which the atria empty of blood after the P-wave. Within the RV-case impedance trace, the period of time during which the ventricles fill with blood during diastole is indicated, as well as the period of rapid ejection of blood during systole.

Returning to FIG. 2, at step 116, the implanted device (or an external system in communication with the device) then assesses, evaluates or monitors diastolic function based on the E-wave parameters and the A-wave parameters derived at steps 100 and 102. As will be explained in detail below, this may be involve pacing the heart of the patient so as to generate an artificial 2:1 block to emphasize the passive and active filling contributions. A 2:1 block is a type of second degree AV block characterized by a delay of atrial impulse conduction to the ventricles through the atrioventricular node. The 2:1 block is discussed, for example, in U.S. Pat. No. 5,601,613 to Florio et al., entitled "Method and Apparatus for Providing Enhanced 2:1 Block Response with Rate-responsive AV Delay in a Pacemaker." At step 118, the implanted device (or an external system in communication with the device) then controls one or more device functions based on the assessment of diastolic function, such as by adjusting the AVD to preferred or optimal values, controlling the storage of diagnostic data pertaining to diastolic function, or controlling the generation of warning signals indicative of detection or progression of any diastolic dysfunction (such as DHF.)

Thus, techniques are provided for using dynamic cardiogenic impedance waveforms to estimate diastolic function of the heart, specifically diastolic flow characterization of passive early filling (equivalent to the echocardiography determined E-wave) and atrial kick (equivalent to the echocardiography determined A-wave).

Exemplary Diastolic Function Monitoring Using Templates

FIGS. 4-7 illustrate an exemplary technique for detecting and tracking diastolic function within a patient based on cardiogenic impedance that exploits certain E-wave and A-wave waveform templates derived for the patient using the aforementioned impedance vectors. In this example, the device identifies two periods of diastolic filling in the different impedance vectors and records impedance during VOO pacing to isolate early diastolic filling from atrial systole. Then, measured diastolic mechanical properties are used to program the AV delay or to track disease state. This procedure can broadly be characterized by four main steps. Step 1: Create a template representative of E-wave morphology from the ventricular impedance signal. Step 2: Create a template representative of A-wave morphology from the atrial impedance signal. Step 3: for each/any state (e.g. a patient state in which diastolic function is useful for diagnosis or a different AV delay setting during CRT optimization), cross-correlate (or convolve) the E and A templates with instantaneously-recorded impedance waveforms to determine the E- and A-wave timing and relative contributions of each in the present state. Step 4: render a determination (diagnosis or programming recommendation) based on the diastolic flow assessment. For example, the device can program the AV delay to avoid E/A fusion while also avoiding A-wave truncation.

Figure 4:
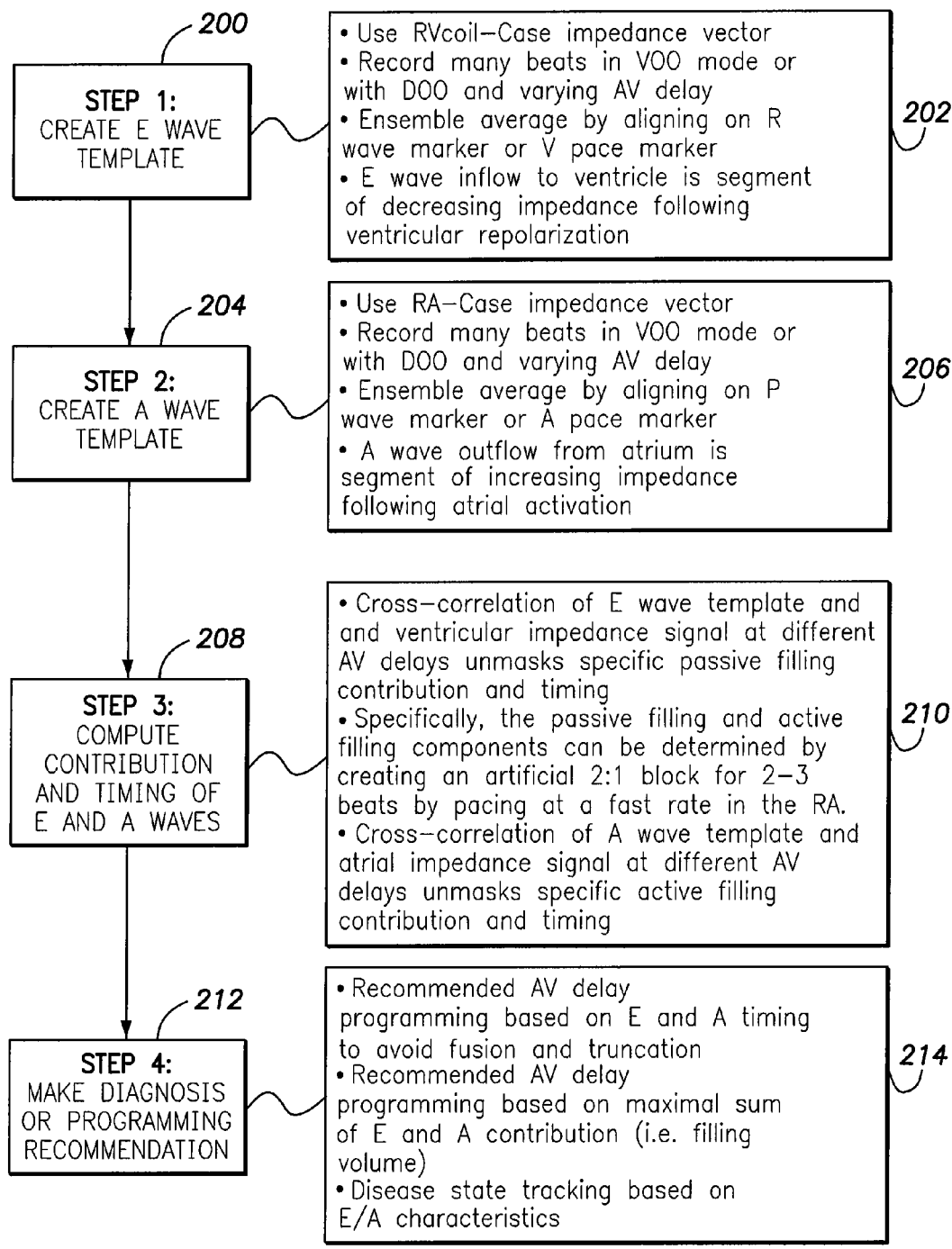
FIG. 4 illustrates an exemplary procedure for assessing diastolic function in accordance with the general technique of FIG. 2, which exploits E-wave and A-wave templates derived during VOO or DOO pacing.

The four main steps are shown in FIG. 4. During the E-wave template generation step 200 (shown in greater detail within block 202), the system generates an E-wave template by: measuring impedance along the RV coil-case impedance vector; recording at least several beats in VOO mode (or with DOO and a varying AV delay); generating an ensemble average by aligning the impedance signals to an R-wave marker or a V-pace marker (detected within a concurrent IEGM or ECG); and then detecting E-wave inflow to the ventricle as a segment of decreasing impedance following a ventricular repolarization event (T-wave) within the corresponding IEGM (or ECG.) During the A-wave template generation step 204 (shown in greater detail within block 206), the device generates an A-wave template by: measuring impedance along the RA-case impedance vector; record at least several beats in VOO mode (or with DOO and varying AV delay); generating an ensemble average by aligning on P-wave marker or A-pace marker; and then detecting A-wave outflow from atrium as a segment of increasing impedance following atrial activation (P-wave.)

Note that the code "VOO" refers to fixed-rate ventricular pacing, which ignores any potentially sensed cardiac signals. This mode is different from various "demand" modes, which only pace when the CRMD determines that the heart is "demanding" pacing. Exemplary demand modes include: DDD, in which the device senses and paces in both the atria and the ventricles and is capable of both triggering and inhibiting functions based upon events sensed in the atria and the ventricles. VDD indicates a mode that senses in both chambers but only paces in the ventricle. A sensed event on the atrial channel triggers a ventricular output after a programmable delay. VVI indicates a mode that paces and senses only in the ventricles and only inhibits functions based upon events sensed in the ventricles. DDI is the same as DDD except that the device only inhibits functions based upon sensed events, rather than triggering functions. As such, the DDI mode is a non-tracking mode precluding its triggering ventricular outputs in response to sensed atrial events. Additional device modes of operation are possible, each represented by standard abbreviations or codes of this type.

During step 208 (shown in greater detail within block 210), the system determines the contribution and timing of E-waves and A-waves by cross-correlating (i.e. convolving) the E-wave template and the ventricular impedance signal at different AV delays to unmask specific passive filling contributions and timing. More specifically, the passive filling and active filling components can be determined by creating an artificial 2:1 block for 2-3 beats by pacing at a fast rate in the RA. Also, the device cross-correlates (i.e. convolves) the A-wave template and the atrial impedance signal at different AV delays to unmask specific active filling contributions and timing. Finally, during step 212 (shown in greater detail within block 214), the system: recommends AV delay programming based on E- and A-wave timing to avoid fusion and truncation; recommends AV delay programming based on a maximal sum of E- and A-wave contributions (i.e. filling volume); and/or tracks the disease state (if any) based on E/A characteristics.

An important aspect of this procedure is the alignment of impedance waveforms to atrial activation, and separately to ventricular activation, using asynchronous VOO pacing (or other suitable non-demand pacing such as DOO.) Note that the ensemble average of RV coil-case impedance beats (aligned by ventricular activation) will have approximately uniformly distributed P-waves, so the contribution from active atrial filling (the A-wave) sums to a substantially negligible level. However, early diastolic filling (the E wave) occurs a fixed time after ventricular activation, and is reflected in the diastolic period averaged RV Coil-case dynamic impedance. The ensemble average of RA-case impedance beats (aligned by atrial activation) will have approximately uniformly distributed ventricular pacing, so any contribution from ventricular activation or relaxation (the E wave) sums to a substantially negligible level. However, active atrial filling of the ventricles (the A-wave) occurs a fixed time after atrial electrical activation, and is reflected in the averaged RA-Case dynamic impedance. This is illustrated within FIG. 5.

Figure 5:
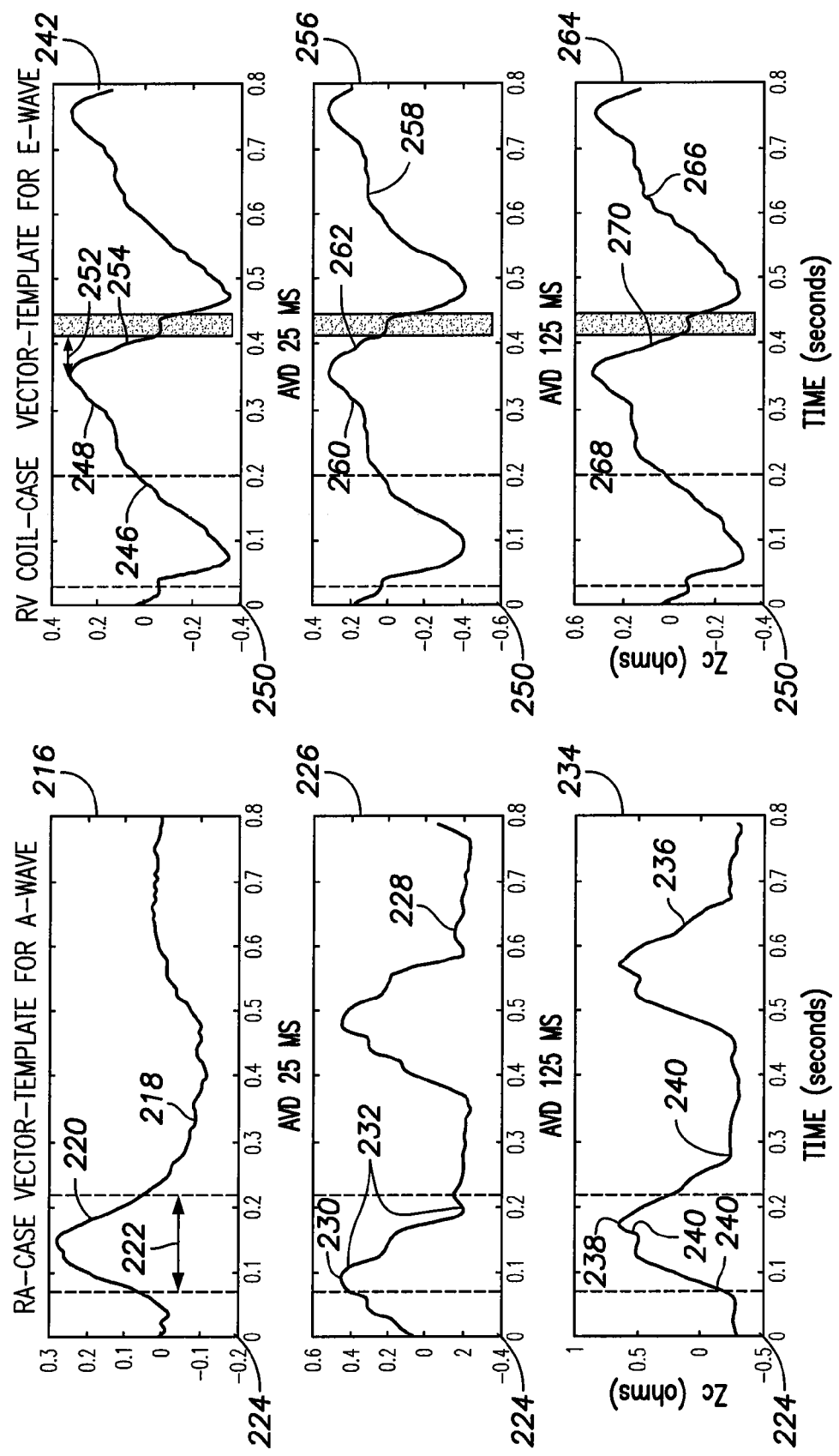
FIG. 5 includes graphs illustrating exemplary cardiogenic impedance traces exploited by the procedure of FIG. 4, particularly illustrating the alignment of E-wave and A-waves with V-pace and A-pace events for various AVD values, including optimal AVD values.

In particular, FIG. 5 provides a set of graphs of impedance templates for both the RA-case vector (i.e. the atrial vector) and the RV coil-case vector (i.e. the ventricular vector) at various AD delay values. More specifically, graph 216 shows an A-wave impedance waveform template 218 with a distinct peak 220 corresponding to the A-wave for the case of no AV pacing delay (i.e. synchronous pacing with AVD of 0 ms.) The duration of the A-wave itself is indicated by line 222. The impedance signal for this (and each of the other RA-case vectors) is "left aligned" on an A-pace/sense event as noted by arrows 224. Graph 226 shows an impedance waveform template 228 with a peak 230 corresponding to the A-wave for asynchronous pacing with a relatively short AVD of 25 ms. A-wave template 228 has a somewhat different morphology than that of template 218. In particular, the A-wave peaks earlier and is terminated sharply before it has completed, as indicated by arrows 232. Graph 234 shows an impedance waveform template 236 with a peak 238 of the A-wave corresponding to asynchronous pacing with a longer (and in this case more optimal) AVD of 125 ms. Within A-wave template 236, the A-wave is tall and broad and not prematurely truncated while also not fused with passive atrial emptying, as indicated by arrows 240.

Turning now to the E-wave templates, graph 242 shows an E-wave impedance waveform template 246 with a distinct peak 248 corresponding to the E-wave for the case of no AV pacing delay. The duration of the E-wave itself is indicated by line 252. The impedance signal for this (and each of the other RV coil-case vectors) is "right aligned" on a V-pace/sense event as noted by arrows 250 (specifically at 0, 400 ms and 800 ms for the three RV coil-case waveforms shown.) Note that a pacing artifact is indicated by arrow 254. Graph 256 shows an impedance waveform template 258 with a peak 260 corresponding to the E-wave for AVD of 25 ms. E-wave template 260 has a slightly different morphology from template 248. In particular, there is a "shoulder" to the peak that represents an undesirable diastasis period after E-wave completion, as indicated by arrow 262. Graph 264 shows an impedance waveform template 266 with a peak 268 corresponding to the E-wave for a longer (and in this case more optimal) AVD of 125 ms. Within E-wave waveform template 268, the E-wave has a smooth profile associated with early filling leading up to the time of V-pace, as indicated by arrow 270.

Further with regard to the procedure of FIGS. 4 and 5, in at least some examples the following detailed implementation parameters are employed. For Steps 1 and 2, templates are generated by ensemble-averaging a plurality of beats. One exemplary embodiment computes the average of the impedance signal from approximately 30 seconds of VOO pacing such that the atrial contribution varies every beat. Another exemplary embodiment records signals at each of many AV delays (for example, a sweep of every 10 ms interval from 40 ms to 200 ms), then computes the ensemble-average of recorded signals across all AV delays, and further compares the templates to each of the recorded AV delay signals.

As noted, alignment of signals when computing the ensemble-average template is important. For the E-wave template of Step 1, the RV coil-case signals are aligned on the R wave or V pace marker to compute the ensemble template, and a duration of 1.5 to 2 cardiac cycles are kept in each member of the ensemble average. Note that some blanking may be necessary after the V-pace due to hardware limitations of measuring impedance immediately after a pacing pulse is delivered. The E-wave will typically manifest between 200-600 ms after the V-pace or R-wave sense;

always after repolarization has begun, as the E-wave represents the ventricular "suction" of atrial blood as well as blood passing through a passive (noncontracting) atrium as a conduit. Thus, the blanking after a pacing pulse may mask the middle or end of the E-wave from the prior beat. The E-wave on the template created in this manner is found from the beginning of the downstroke of impedance during diastole (impedance decreases as atrial blood flows into the ventricle) until the beginning of the upstroke of impedance shortly after ventricular activation (impedance increases as blood is ejected from the ventricle). With varying AV delays, the E-wave may be fused with or masked by active atrial contribution, ventricular ejection, and/or valve insufficiencies, and thus the ensemble represents an idealized E-wave morphology and timing in respect to ventricular activation, to be used as a reference signal in Step 3.

Similarly, for the A-wave template in Step 2, the RA-case signals are aligned on the P-wave or A-pace marker to compute the ensemble template, and a duration of 1 to 1.5 cardiac cycles are kept in each member of the ensemble average. Note that some blanking may be necessary after the A-pace due to hardware limitations of measuring impedance immediately after a pacing pulse is delivered. The A-wave will typically manifest between 50-200 ms after the A-pace or P-wave sense, after sufficient time (e.g. 80 ms) for much of the atrium to be depolarized and account for electro-mechanical delay, since A-wave represents the atrial kick or active atrial emptying to ventricle. Thus, the blanking period may be substantially before the A-wave of interest on the impedance signal. The A-wave on the template created in this manner is found from the beginning of the upstroke of impedance during atrial systole (impedance increases as blood is ejected from the atrium into the ventricle) until the flat or downstroke thereafter (impedance increases as circulating blood returns to the atrium and/or regurgitant blood from the ventricle fills the atrium). With varying AV delays, the A-wave may be fused with the E-wave or truncated by ventricular activation, and thus the ensemble represents an idealized A-wave morphology and timing in respect to atrial activation, to be used as a reference signal in Step 3.

In Step 3, the template E-wave is correlated against a ventricular impedance signal from a candidate beat to be used for programming test or diagnosis. The time/phase shift resulting in the greatest correlation coefficient is taken as the E-wave timing for that particular beat. The degree/value of that peak correlation is a relative metric of the strength of the E-wave or the blood received by the ventricle. Another method to corroborate the strength of the E-wave is to compare this with atrial filling. Also in Step 3, the template A-wave is correlated against an atrial impedance signal from a candidate beat to be used for programming test or diagnosis. The time/phase shift resulting in the greatest correlation coefficient is taken as the A-wave timing for that particular beat. The degree/value of that peak correlation is a relative metric of the strength of the A-wave or the blood ejected by the atrium.

In Step 4, depending on the purpose, various results are applied. In the case of AV timing optimization, an AV delay is preferably chosen among several tested that provides E and A-wave timing resulting in no truncation of the A-wave (i.e. AVD not too short) and also in no fusion of the E and A-waves (i.e. AVD not too long.) This is illustrated in FIG. 5 by comparing the middle and bottom graphs. Secondarily, among more than one option fulfilling the timing optimization criteria listed, the AVD providing the largest E and A correlation coefficients with the respective templates is chosen, with the rationale that this configuration has the largest blood volume entering the ventricle before ejection.

Note that the RA-case and RV coil-case vectors most closely represent trans-tricuspid flow, whereas pacing timing optimization is generally performed by inspecting trans-mitral flow. Hence, in one scenario, given normal biatrial conduction and either normal biventricular conduction or fixed biventricular pacing, the right-sided valve timings are a fair approximation of the left-sided valve timings. In an alternative embodiment, the impedance vectors employed are the proximal LV-case instead of the RA-case, which has a receptive field in the vicinity of the left atrial appendage and mitral valve plane, and the distal LV-case instead of the RV coil-case, which has a receptive field in the LV.

Turning now to FIGS. 6 and 7, an alternative flow-chart representation of the embodiment of FIGS. 4 and 5 is presented. As this embodiment has already been described in detail, the steps of FIGS. 6 and 7 will only be described briefly herein below. Within FIG. 6, E-wave template generation and processing is presented in flowchart form. Beginning at step 300, during a setup procedure performed by the implanted device (or by an external system in communication with the device), the device generates an E-wave impedance template representative of passive filling of the ventricles based on ventricular Zc (i.e. RV coil-case) values by: measuring ventricular Zc values during a period of non-demand pacing over a set of cardiac cycles (e.g. 30 secs) or during vent. pacing during AF or during AMS; detecting ventricular activation events (V-pulse/V-sense) within the cardiac cycles (with suitable blanking); aligning the measured ventricular Zc values to detected activation events of corresponding cycles such that there are approximately uniformly distributed P-waves so the contribution from active atrial filling sums to a substantially negligible level; ensemble averaging the aligned ventricular Zc values (including a duration of 1.5 to 2 cardiac cycles); detecting T-waves within corresponding cardiac cycles; identifying a segment of decreasing Zc within the ensemble averaged ventricular Zc values following corresponding T-waves within the cardiac cycles (such as from the beginning of the downstroke of Zc during diastole until beginning of the upstroke shortly after ventricular activation); and then storing the segment of decreasing Zc as an E-wave template. Thereafter, in use, the device at step 302 measures additional ventricular Zc values (representative of passive filling) during newly-detected cardiac cycles. At step 304, the device (or an external system in communication with the device) then determines the convolution (such as by calculating the cross-correlation) of the E-wave template with the additional ventricular Zc values (or determines or derives some other similar measure of the similarity of the two waveforms) to derive E-wave parameters representative of passive filling contributions to diastolic function within the newly-detected cardiac cycles (with the time/phase shift resulting in greatest correlation coefficient indicating E-wave timing and degree/value of peak correlation providing a relative metric of the strength of E-wave.) Additionally or alternatively, parameters representative of the amount of blood received by the ventricles during passive filling are determined based on a metric value obtained by calculating the integral of the ventricular impedance values of the subsequent cardiac cycle for samples where a correlation coefficient between the E-wave impedance template and the ventricular impedance values of the subsequent cardiac cycle exceeds a predetermined threshold. In this regard, peak impedance may be one preferred metric, while the integral of the impedance is another preferred metric, and the system may then to integrate over the entire E-wave match. Diagnosis and/or programming recommendations may then be made, as already described with reference to Step 4 of FIG. 4.

Within FIG. 7, A-wave template generation and processing is presented in flowchart form. Beginning at step 350, during the setup procedure performed by the implanted device (or by the external system), the device generates an A-wave impedance template representative of active filling of the ventricles based on atrial Zc values (i.e. RA-case) by: measuring atrial Zc values during a period of non-demand pacing over a set of cardiac cycles (e.g. 30 secs); detecting atrial activation events (A-pulse/A-sense) within the cardiac cycles (with suitable blanking); aligning the measured atrial Zc values to detected atrial activation events of corresponding cycles such that V-pace/V-sense events are approximately uniformly distributed so the contribution from ventricular activation and relaxation (i.e. the E-wave) sums to a substantially negligible level; ensemble averaging the aligned atrial Zc values (including a duration of 1 to 1.5 cardiac cycles); identifying a segment of increasing Zc within the ensemble averaged atrial Zc values following corresponding A-pulse/A-sense within the cardiac cycles (such as from the beginning of the upstroke of Zc during atrial systole until the subsequent flat or downstroke portion); and then storing the segment of decreasing Zc as A-wave template. Thereafter, in use, the device at step 353 measures additional atrial Zc values (representative of active filling of ventricles) during newly-detected cardiac cycles. At step 354, the device (or an external system in communication with the device) then determines the convolution (e.g. cross-correlation) of the A-wave template with the additional atrial Zc values to derive A-wave parameters representative of active filling contributions to diastolic function within the newly-detected cardiac cycles (with the time/phase shift resulting in greatest correlation coefficient indicating A-wave timing and degree/value of peak correlation providing a relative metric of the strength of A-wave.) Additionally or alternatively, the parameters representative of the amount of blood received by the ventricles during active filling are determined based on a metric value obtained by calculating the integral of the atrial impedance values of the subsequent cardiac cycle for samples where the correlation coefficient between the A-wave impedance template and the atrial impedance values of the subsequent cardiac cycle exceeds a predetermined threshold. Diagnosis and/or programming recommendations may then be made, as already described above.

Alternative Diastolic Function Monitoring Technique

Figure 8:
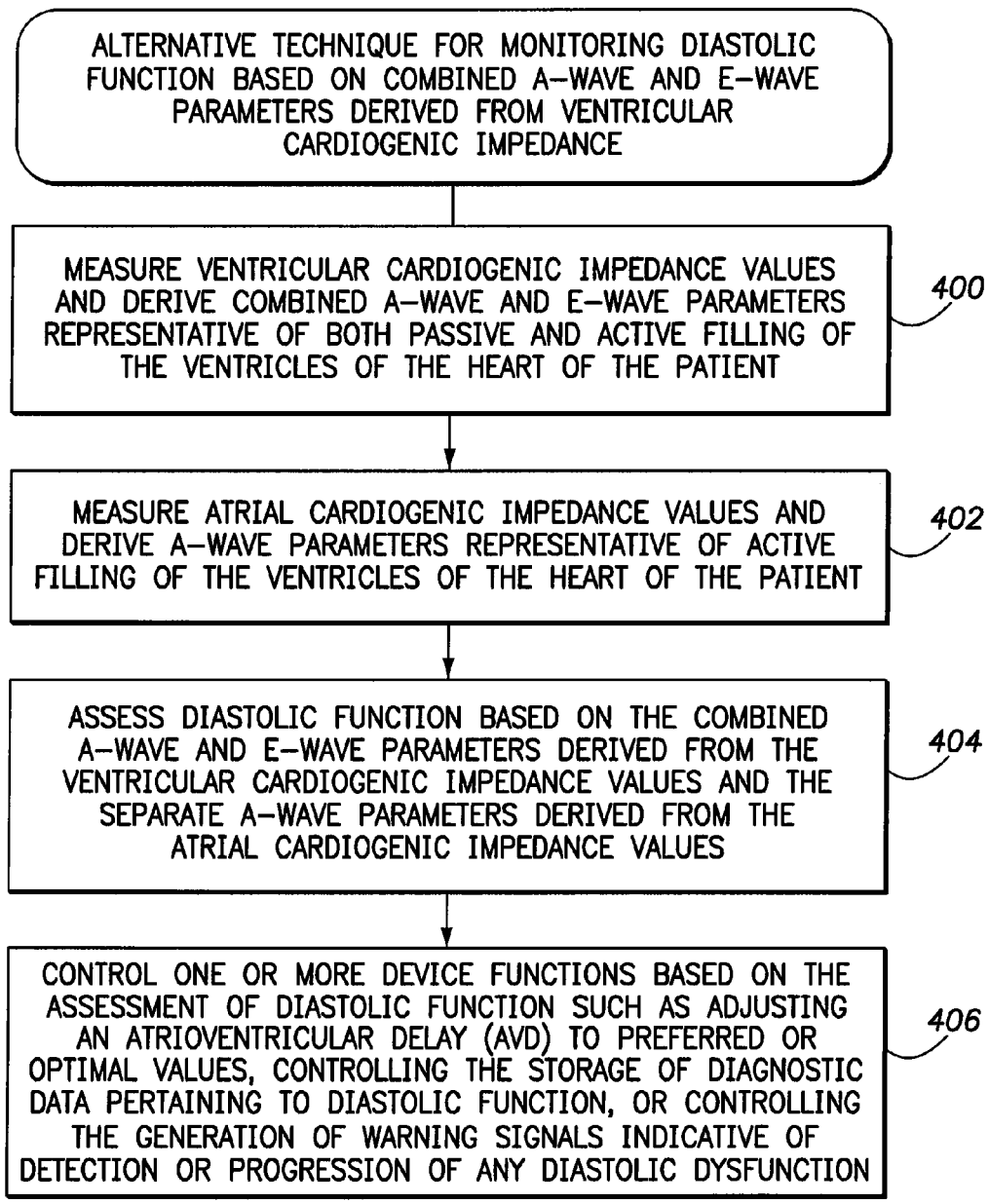
FIG. 8 illustrates an alternative procedure for assessing diastolic function in accordance with the general technique of FIG. 2, which exploits combined E-wave and A-wave contributions derived from an RV-case impedance vector.
Figure 9:
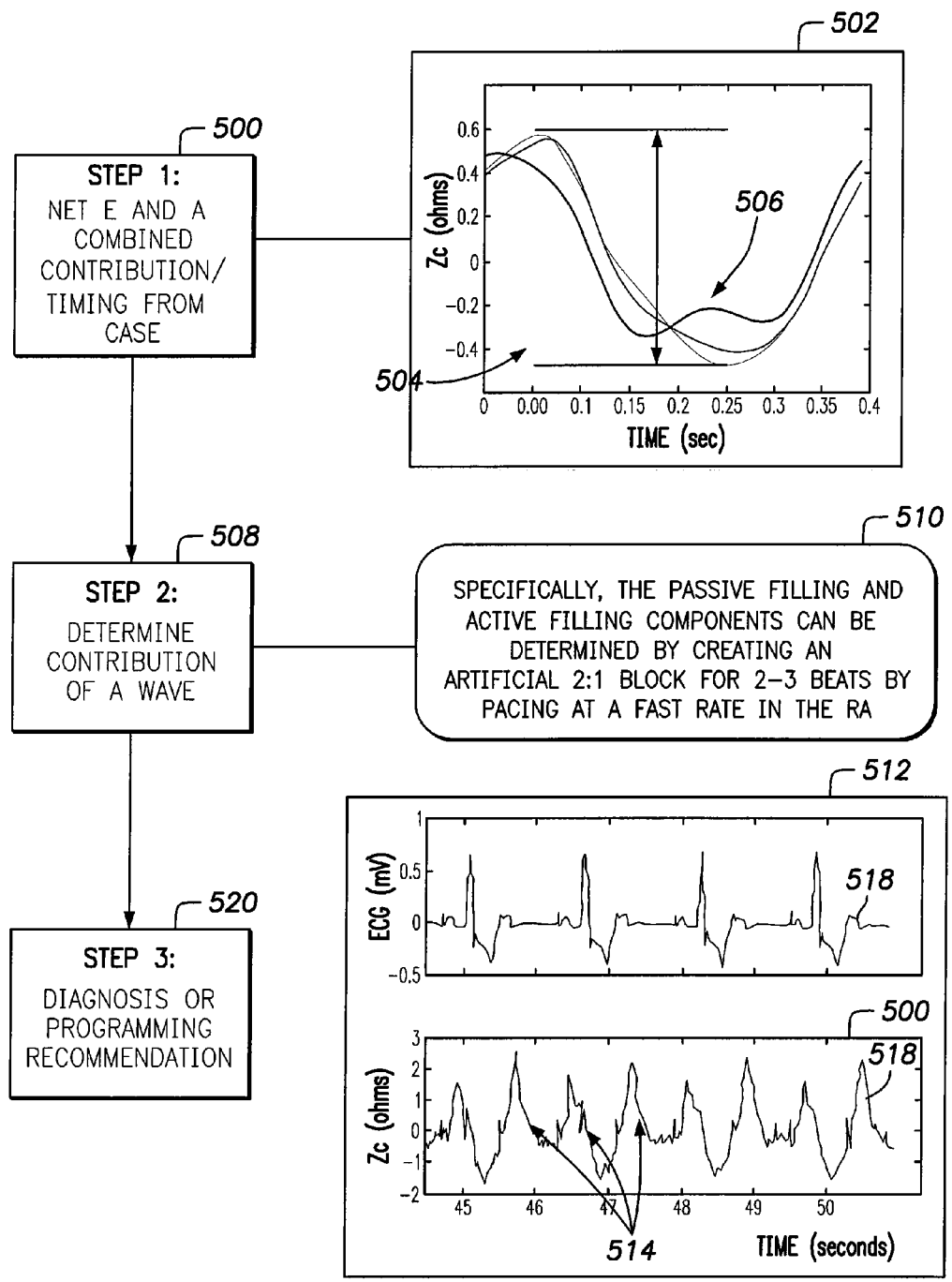
FIG. 9 is a hybrid diagram including graphs illustrating exemplary cardiogenic impedance traces exploited by the technique of FIG. 8, particularly illustrating the effect of an artificial 2:1 block.

FIGS. 8-9 illustrate an alternative technique for detecting and tracking diastolic function based on cardiogenic impedance wherein combined E-wave/A-wave information is derived from the ventricular impedance signals. That is, in this example, the net ventricular filling of combined E- and A-waves is extracted from the morphology of RV-case vector. The technique is summarized in FIG. 8, with further details provided within FIG. 9.

Beginning at step 400 of FIG. 8, the implanted device, measures ventricular cardiogenic impedance values (such as along the RV coil-case vector) and derives combined A-wave and E-wave parameters representative of both passive and active filling of the ventricles of the heart of the patient. At step 402, the device measures atrial cardiogenic impedance values (such as along the RA-case vector) and derives A-wave parameters representative of active filling of the ventricles of the heart of the patient. At step 404, the device (or an external system in communication with the device) assesses diastolic function based on the combined A-wave and E-wave parameters derived from the ventricular cardiogenic impedance values and the separate A-wave parameters derived from the atrial cardiogenic impedance values. At step 406, the device then controls one or more device functions based on the assessment of diastolic function, such as by adjusting AVD to preferred or optimal values, as discussed above. Note that, although steps 400 and 402 are shown sequentially, these steps may be performed concurrently (subject to the capabilities of the device itself) or in the opposite order.

Turning now to FIG. 9, exemplary implementation details are illustrated. At step 500, the net E- and A-wave combined contribution/timing is derived from the RV-case Zc signal. Exemplary Zc is illustrated in graph 502 by way of traces 504. More specifically, trace 506 represents a suboptimal (i.e. too short) AV delay with low ventricular diastolic filling (resulting from low atrial contribution). The other two traces represent increasingly optimal AV delays of 60 ms and 80 ms, wherein the ventricular diastolic filling is expected to be more optimal, as evidenced by the longer electro-mechanical delay and the increased amplitude of the impedance signal as well as the reduction of the atrial diastasis. At step 508, the contribution from the A-wave is determined by creating a 2:1 block and then examining the resulting atrial Zc waveform. As indicated within block 510, this may be accomplished for example by overdrive pacing the atrium and/or by prolonging the ventricular or AV refractory period in patients with intact conduction and is easily accomplished by double-pacing the atrium in patients with high-degree or complete AV block. Once 2:1 electrical conduction is established (for a transient of 2-3 beats), the A-wave contribution is isolated by signal common to the RA-case vector following atrial beats with and those beats without ventricular tracking. In graph 512, this is indicated by the upward deflections 514 (i.e. atrial emptying viewed by RA-Case vector) within the impedance signal 516. A corresponding ECG trace 518 is also shown. At step 520, after measurement of quantities representing the A-wave in isolation and the combined E- and A-wave, a diagnosis or programming recommendation may be delivered as with the embodiments described above.

Thus, various exemplary techniques have been described for assessing diastolic function and programming AV delays to preferred or optimal values. It should be understood that any preferred, target or optimal values obtained using techniques described herein are not necessarily absolutely optimal in a given quantifiable or mathematical sense. What constitutes "optimal" depends on the criteria used for judging the resulting performance, which can be subjective in the minds of clinicians. The AV delay values (and other control parameters) identified or selected using the techniques described herein represent, at least, a "preferred" set of parameters. Clinicians may choose to adjust or alter the control parameters at their discretion using suitable external control devices.

Note also that the diastolic function assessment techniques described herein can be supplemented or corroborated with other assessment techniques (depending upon the capabilities of the device/system.) See, for example, techniques described in the following patents and patent applications: U.S. Pat. No. 8,280,523 to Keel et al., entitled "System and Method for Monitoring Diastolic Function using an Implantable Medical Device"; U.S. Pat. No. 7,662,086 to Bjorling, entitled "Detection and/or Monitoring of Diastolic Heart Failure"; U.S. Pat. No. 7,526,338 to Gill et al., entitled "Implantable Cardiac Device for Monitoring Diastolic Heart Failure and Method of Operation and Use Thereof"; U.S. Pat. No. 7,850,616 to Gill et al., entitled "Determination of Diastolic Heart Failure"; U.S. Pat. No. 7,959,576 to Torpo et al., entitled "Apparatus for Detecting Diastolic Heart Failure"; U.S. Pat. No. 8,285,377 to Rosenberg et al., entitled "Pacing, Sensing and Other Parameter Maps based on Localization System Data"; U.S. Pat. No. 8,326,419 to Rosenberg et al., entitled "Therapy Optimization via Multi-Dimensional Mapping"; U.S. Pat. No. 7,662,086 of Bjorling, entitled "Detection and/or Monitoring of Diastolic Heart Failure"; U.S. Patent Application 2011/0054560 of Rosenberg et al., entitled "Pacing, Sensing and Other Parameter Maps Based on Localization System Data"; U.S. Patent Application 2011/0060230 to Gill et al., entitled "Determination of Diastolic Heart Failure"; U.S. Pat. No. 8,412,327 of Hou et al., entitled "Cardiac Resynchronization Therapy Optimization Using Vector Measurements Obtained From Realtime Electrode Position Tracking"; and U.S. Patent Application 2011/0319954 of Niazi et al., entitled "Metrics and Techniques for Optimization of Cardiac Therapies." See, also, U.S. patent application Ser. No. 13/571,235 of Muller, filed Aug. 9, 2012, entitled "System and Method for Left Atrial Pacing in Patients with Diastolic Heart Failure."

For the sake of completeness, a detailed description of an exemplary CRMD for performing these techniques will now be provided. However, principles of invention may be implemented within other CRMD implementations or within other implantable devices such as stand-alone diastolic function monitoring devices, CRT devices or ICDs. Furthermore, although examples described herein involve processing of diastolic function data by the implanted device itself, some or all of the operations may be performed using an external device, such as a bedside monitor, device programmer, computer server or other external system based on impedance data detected by the CRMD and then transmitted to the external device. Processing by the implanted device itself is preferred in at least some implementations since that allows the device to promptly detect the onset of diastolic dysfunction and to issue prompt warnings (if warranted.)

Exemplary CRMD

Figure 10:
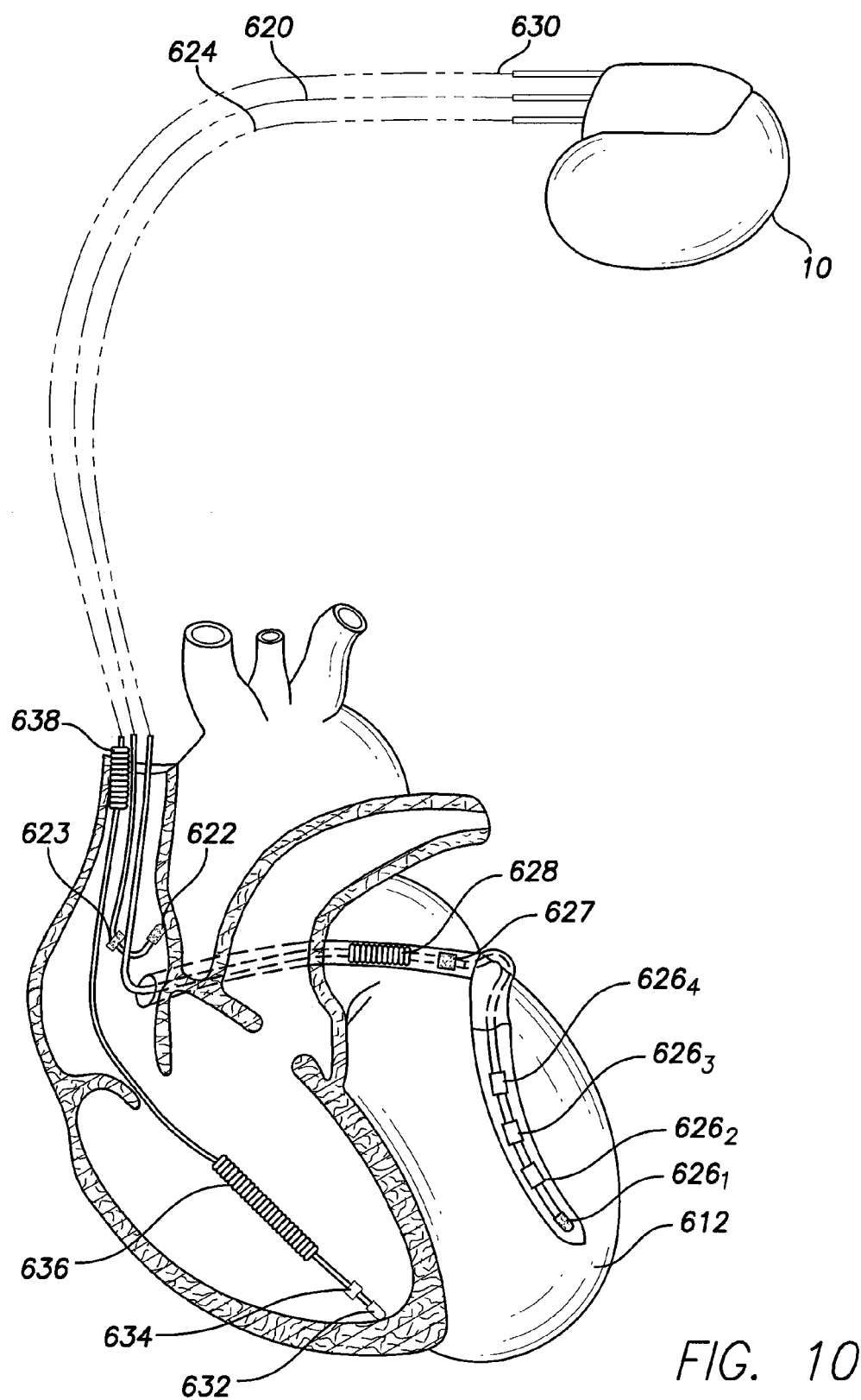
FIG. 10 is a simplified, partly cutaway view, illustrating the device of FIG. 1 along with a set of leads implanted in the patient.
Figure 11:
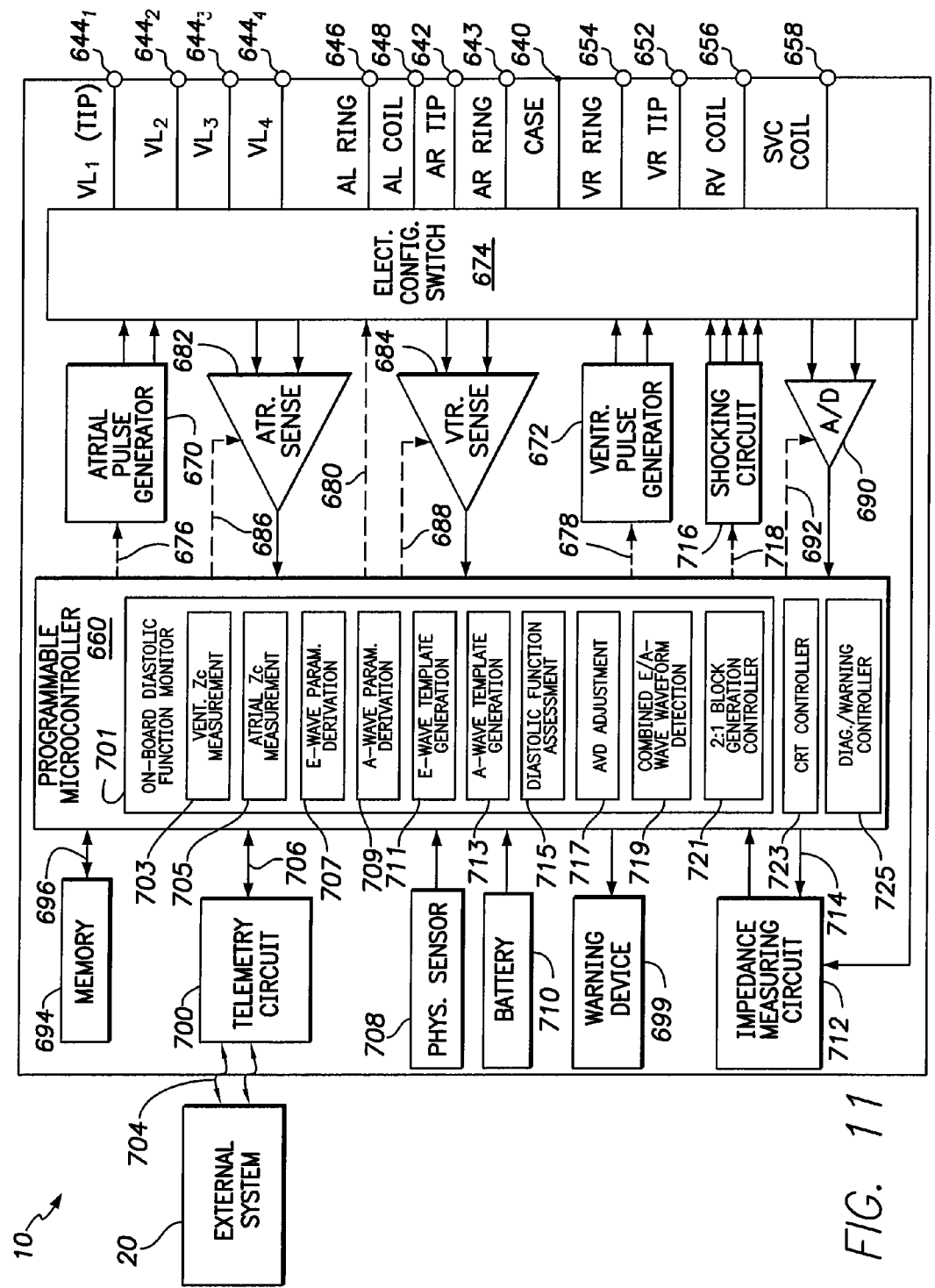
FIG. 11 is a functional block diagram of the device of FIG. 10, illustrating circuit elements that provide cardioversion, defibrillation and/or pacing stimulation in the heart and particularly illustrating components for assessing or evaluating diastolic function using techniques of FIGS. 2-9.

With reference to FIGS. 10 and 11, an exemplary CRMD will now be described where the device is equipped with an on-board diastolic function monitor. FIG. 10 provides a simplified block diagram of the CRMD, which is a dual-chamber stimulation device capable of treating both fast and slow arrhythmias with stimulation therapy, including cardioversion, defibrillation and pacing stimulation, including CRT stimulation using a quad-pole LV lead. To provide atrial chamber pacing stimulation and sensing, CRMD 10 is in electrical communication with a heart 612 by way of a left atrial lead 620 having an atrial tip electrode 622 and an atrial ring electrode 623 implanted in the atrial appendage. CRMD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. The SVC coil electrode, as with many lead components, is optional. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 10 is coupled to an LV lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 624 is designed to receive atrial and ventricular cardiac signals and to deliver left ventricular pacing therapy using a set of four left ventricular electrodes $626_1$, $626_2$, $626_3$, and $626_4$ (thereby providing a quadripole lead), left atrial pacing therapy using at least a left atrial ring electrode 627, and shocking therapy using at least a left atrial coil electrode 628 implanted on or near the left atrium. In other examples, more or fewer LV electrodes are provided. Although only three leads are shown in FIG. 10, it should also be understood that additional leads (with one or more pacing, sensing and/or shocking electrodes) might be used and/or additional electrodes might be provided on the leads already shown, such as additional electrodes on the RV lead. Note that, on present commercially-available hardware, there is often no separate electrode 627.

A simplified block diagram of internal components of CRMD 10 is shown in FIG. 11. While a particular CRMD is shown, this is for illustrative purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for CRMD 10, shown schematically in FIG. 11, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, $644_1$-$644_4$, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing and pacing, the connector includes, at least, left ventricular tip and ring terminals 644 and 645, respectively.

The connector also includes a left atrial ring terminal ($A_L$ RING) 646 and a left atrial shocking terminal ($A_L$ COIL) 648, which are adapted for connection to the left atrial ring electrode 627 and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal (RV COIL) 656, and an SVC shocking terminal (SVC COIL) 658, which are adapted for connection to the RV tip electrode 632, right ventricular ring electrode 634, the $V_R$ coil electrode 636, and the SVC coil electrode 638, respectively.

At the core of CRMD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 11, an atrial pulse generator 670 and a ventricular pulse generator 672 generate pacing stimulation pulses for delivery by the right atrial lead 620, the right ventricular lead 630, and/or the LV lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 682 and ventricular sensing circuits 684 may also be selectively coupled to the right atrial lead 620, LV lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are capable of triggering or inhibiting the atrial and ventricular pulse generators, 670 and 672, respectively, in a demand fashion in response to the absence or presence of cardiac activity in the appropriate chambers of the heart.

For arrhythmia detection, CRMD 10 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 690. The data acquisition system 690 is configured to acquire the IEGM signals, convert the raw analog data into a digital signal, and store the digital signals for later processing and/or telemetric transmission to an external device 16. The data acquisition system 690 is coupled to the right atrial lead 620, the LV lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of CRMD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 694 through a telemetry circuit 700 in telemetric communication with the external device 116, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of CRMD 100 (as contained in the microcontroller 660 or memory 694) to be sent to the external device 116 through an established communication link 704. CRMD 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, VV delay, etc.) at which the atrial and ventricular pulse generators, 670 and 672, generate stimulation pulses. While shown as being included within CRMD 10, it is to be understood that the physiologic sensor 708 may also be external to CRMD 10, yet still be implanted within or carried by the patient. A common type of rate responsive sensor is an activity sensor incorporating an accelerometer or a piezoelectric crystal, which is mounted within the housing 640 of CRMD 10. Other types of physiologic sensors are also known, for example, sensors that sense the oxygen content of blood, respiration rate and/or minute ventilation, pH of blood, ventricular gradient, contractility, photoplethysmography (PPG), heart sounds, etc. It should be understood that multiple separate sensors can be provided and, depending upon the parameter to be detected, at least some of the sensors might be positioned external to the device housing.

The CRMD additionally includes a battery 710, which provides operating power to all of the circuits shown in FIG. 10. The battery 710 may vary depending on the capabilities of CRMD 10. If the system only provides low voltage therapy, a lithium iodine or lithium copper fluoride cell typically may be utilized. For CRMD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 11, CRMD 10 has an impedance measuring circuit 712, enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the motion of heart valves; and detecting cardiogenic impedance for use in assessing diastolic function, etc. Impedance measuring circuit 712 is coupled to switch 674 so that any desired electrode may be used.

In the case where CRMD 10 is intended to operate as an ICD device, it detects the occurrence of an arrhythmia requiring a shock, and automatically applies an appropriate electrical shock therapy to the heart aimed at terminating the arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules or more), delivered asynchronously (since R-waves may be too disorganized), and pertaining exclusively to the treatment of fibrillation. Accordingly, the microcontroller 660 is capable of controlling synchronous or asynchronous delivery of shocking pulses.

An internal warning device 699 may be provided for generating perceptible warning signals to the patient pertaining to diastolic dysfunction or other issues. The warning signals are generated via vibration, voltage or other methods.

Insofar as diastolic function assessment is concerned, the microcontroller includes an on-board diastolic function monitor 701 operative to perform or control the diastolic function monitoring functions described above. In this example, the diastolic function monitor includes: a ventricular Zc measurement system 703 operative to control the measurement of ventricular cardiogenic impedance values and an atrial Zc measurement system 705 operative to control the measurement of atrial cardiogenic impedance values. An E-wave parameter derivation system 707 is operative to derive E-wave parameters representative of passive filling of the ventricles of the heart of the patient from the ventricular cardiogenic impedance values. An A-wave parameter derivation system 709 is operative to derive A-wave parameters representative of active filling of the ventricles of the heart of the patient from the ventricular cardiogenic impedance values. Based on the derived parameters, an E-wave template generation system 711 is operative to generate an E-wave template. An A-wave template generation system 713 is operative to generate an A-wave template. A diastolic function assessment system 715 is operative to assess diastolic function based on the E-wave parameters and the A-wave parameters (e.g., in comparison with the corresponding templates.) An AVD adjustment system 717 adjusts AVD values in an effort to optimize the values (or during the generation of the aforementioned templates, as described above.) In some examples, a combined E/A-wave waveform detection system 719 is used. (See, for example, the embodiment of FIGS. 8 and 9.) Also, in some examples, the CRMD operates to generate an artificial 2:1 block using 2:1 block generation controller 721. A CRT controller 723 may be provided to control CRT. Diagnostics and/or warnings may be generated by controller 725.

Depending upon the implementation, the various components of the microcontroller may be implemented as separate software modules or the modules may be combined to permit a single module to perform multiple functions. Although shown as components of the microcontroller, some or all of the components may be implemented separately from the microcontroller, using application specific integrated circuits (ASICs) or the like. As already explained, some or all of the techniques described herein can be performed by (or under the control of) an external device. Accordingly, an exemplary external programmer device will now also be described.

Exemplary External Programmer Device

Figure 12:
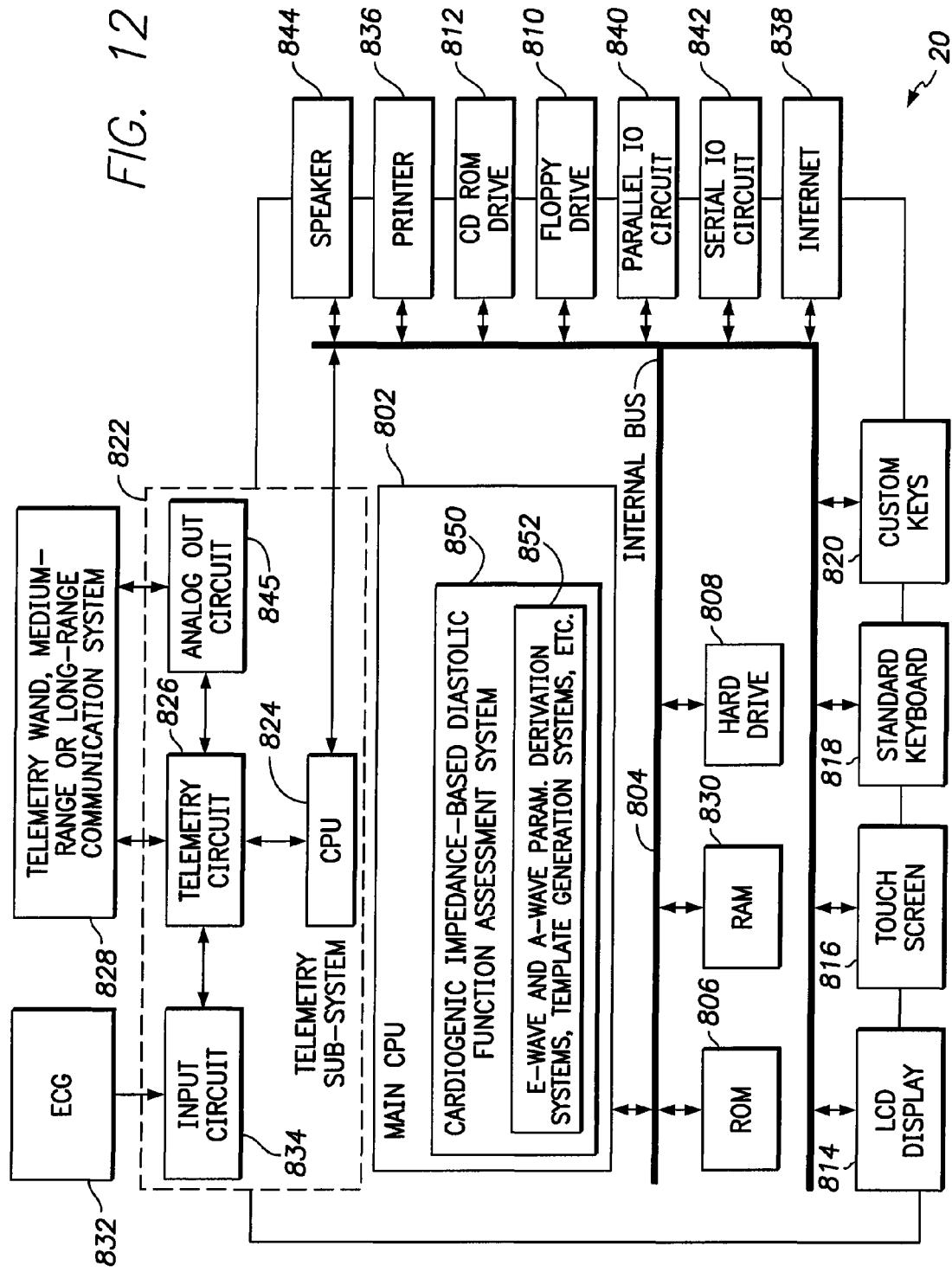
FIG. 12 is a functional block diagram illustrating components of the external programmer of FIG. 1, particularly illustrating components for controlling the systems and techniques of FIGS. 1-9.

FIG. 12 illustrates pertinent components of an external programmer 20 for use in interrogating and programming the CRMD of FIGS. 10 and 11 and for performing the above-described diastolic function assessment. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (ECG or EKG) data from separate external ECG leads that may be attached to the patient. Depending upon the specific programming of the external programmer, programmer 20 may also be capable of processing and analyzing data received from the implanted device and from the EKG leads to, for example, render preliminary diagnosis as to medical conditions of the patient or to the operations of the implanted device.

Now, considering the components of programmer 20, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Insofar as diastolic function is concerned, main CPU 802 includes a cardiogenic impedance-based diastolic function assessment system 850 operative to perform the assessment described above based on impedance data received from the CRMD. System 850 includes components corresponding to some or all of the components of the on-board monitor of FIG. 11, such as E-wave and A-wave parameter derivation systems, template generation systems, etc. In response to the diastolic function assessment, the clinician enters various programming commands via either a touch screen 816 overlaid on the LCD display or through a standard keyboard 818 supplemented by additional custom keys 820, such as an emergency VVI (EVVI) key. (The EVVI key sets the implanted device to a safe VVI mode with high pacing outputs. This ensures life sustaining pacing operation in nearly all situations but by no means is it desirable to leave the implantable device in the EVVI mode at all times.)

Typically, the clinician also controls the programmer 20 to retrieve other data stored within the CRMD and to also retrieve ECG data from ECG leads, if any, coupled to the patient. To this end, CPU 802 transmits appropriate signals to a telemetry subsystem 822, which provides components for directly interfacing with the implanted devices, and the ECG leads. Telemetry subsystem 822 may include its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to communication system 828, which may include a telemetry wand, medium-range or long-range RF communication system, which, in turn, receives and transmits signals electromagnetically from the telemetry unit of the implanted device. (If a short-range telemetry wand is employed, it is placed over the chest of the patient near the implanted device to permit reliable transmission of data between the telemetry wand and the implanted device.) The telemetry subsystem is shown as also including an input circuit 834 for receiving surface ECG signals from surface ECG system 832. In other implementations, no ECG circuit is provided.

Typically, the external programming device controls the implanted devices via appropriate signals generated by the telemetry system to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted devices is stored by external programmer 20 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 20, the implanted devices may be further controlled to transmit additional data in real time as it is detected by the implanted device, such as additional IEGM data, lead impedance data, and the like. Additionally, or in the alternative, telemetry subsystem 822 receives ECG signals from ECG leads 832 via an ECG processing circuit 834. As with data retrieved from the implanted device itself, signals received from the ECG leads are stored within one or more of the storage devices of the external programmer. Typically, ECG leads output analog electrical signals representative of the ECG. Accordingly, ECG circuit 834 includes analog to digital conversion circuitry for converting the signals to digital data appropriate for further processing within the programmer. Depending upon the implementation, the ECG circuit may be configured to convert the analog signals into event record data for ease of processing along with the event record data retrieved from the implanted device. Typically, signals received from the EGG leads are received and processed in real time.

Thus, in this example, the programmer receives data both from the implanted device and from optional external ECG leads. Data retrieved from the implanted devices includes parameters representative of the current programming state of the implanted devices. Under the control of the clinician, the external programmer displays the current programmable parameters and permits the clinician to reprogram the parameters. To this end, the clinician enters appropriate commands via any of the aforementioned input devices and, under control of CPU 802, the programming commands are converted to specific programmable parameters for transmission to the implanted device via telemetry system 828 to thereby reprogram the implanted device. Prior to reprogramming specific parameters, the clinician may control the external programmer to display any or all of the data retrieved from the implanted device or from the ECG leads, including displays of ECGs, IEGMs, and statistical patient information. Any or all of the information displayed by programmer may also be printed using a printer 836.

Programmer/monitor 20 also includes an internet connection 838 to permit direct transmission of data to other programmers via the public switched telephone network (PSTN) or other interconnection line, such as a T1 line, fiber optic cable, Wi-Fi, cellular network, etc. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the clinician. Telemetry subsystem 822 additionally includes an analog output circuit 845 for controlling the transmission of analog output signals, such as IEGM signals output to an ECG machine or chart recorder.

With the programmer configured as shown, a clinician or other user operating the external programmer is capable of retrieving, processing and displaying a wide range of information received from the implanted device and to reprogram the implanted device if needed. The descriptions provided herein with respect to FIG. 12 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular exemplary embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient, the method comprising:
    measuring values representative of ventricular cardiogenic impedance and deriving E-wave parameters representative of passive filling of the ventricles of the heart of the patient from the ventricular cardiogenic impedance values, wherein deriving E-wave parameters from the ventricular cardiogenic impedance values includes:
        generating an E-wave impedance template representative of passive filling of the ventricles based on ventricular cardiogenic impedance values measured during an initial period of non-demand pacing, with the period of non-demand pacing including atrial pacing at a rate sufficient to trigger an artificial 2:1 block to emphasize active and passive filling contributions to diastolic function;
        measuring additional values representative of ventricular impedance during a subsequent cardiac cycle to be examined; and
        determining a convolution of the E-wave impedance template with the additional ventricular impedance values to derive E-wave parameters representative of passive filling contributions to diastolic function within the subsequent cardiac cycle;
    measuring values representative of atrial cardiogenic impedance and deriving A-wave parameters representative of active filling of the ventricles from the atrial cardiogenic impedance values;
    assessing diastolic function based on the E-wave parameters and the A-wave parameters; and
    controlling at least one device function based on the assessment of diastolic function.

2. The method of claim 1 wherein measuring values representative of ventricular cardiogenic impedance includes measuring cardiogenic impedance along a vector between a right ventricular (RV) electrode and a housing of the device.

3. The method of claim 1 wherein measuring values representative of atrial cardiogenic impedance includes measuring cardiogenic impedance along a vector between a right atrial (RA) electrode and a housing of the device.

4. The method of claim 1 wherein the E-wave parameters representative of passive filling contributions to diastolic function include a parameter representative of the timing of the E-wave.

5. The method of claim 4 wherein the timing of the E-wave of the subsequent cardiac cycle is determined based on a time shift resulting in a greatest correlation coefficient between the E-wave impedance template and the ventricular impedance values of the subsequent cardiac cycle.

6. The method of claim 5 wherein the E-wave parameters include parameters representative of an amount of blood received by the ventricles during the particular cardiac cycle due to passive filling.

7. The method of claim 6 wherein the parameters representative of the amount of blood received by the ventricles during passive filling are determined based on a peak metric value of the greatest correlation coefficient between the E-wave impedance template and the additional ventricular impedance values of the subsequent cardiac cycle.

8. The method of claim 6 wherein the parameters representative of the amount of blood received by the ventricles during passive filling are determined based on a metric value obtained by calculating an integral of the ventricular impedance values of the subsequent cardiac cycle for samples where a correlation coefficient between the E-wave impedance template and the ventricular impedance values of the subsequent cardiac cycle exceeds a predetermined threshold.

9. The method of claim 1 wherein generating the E-wave impedance template includes:
    measuring values representative of ventricular cardiogenic impedance during a period of non-demand pacing comprising a plurality of cardiac cycles;
    detecting ventricular activation events within the cardiac cycles;
    aligning the measured ventricular cardiogenic impedance values to the detected ventricular activation events of corresponding cardiac cycles such that any corresponding atrial activation events are approximately uniformly distributed so a contribution from active atrial filling sums to a substantially negligible level;
    ensemble averaging the aligned ventricular cardiogenic impedance values;
    detecting corresponding ventricular repolarization events within the cardiac cycles;
    identifying a segment of decreasing impedance within the ensemble averaged ventricular cardiogenic impedance values following corresponding ventricular repolarization events within the cardiac cycles; and
    storing the segment of decreasing impedance as the E-wave template.

10. The method of claim 1 wherein the period of non-demand pacing includes VOO pacing.

11. The method of claim 1 wherein the period of non-demand pacing includes DOO pacing with a selected atrio-ventricular (AV) pacing delay.

12. The method of claim 1 wherein the period of non-demand pacing includes ventricular pacing during one or more of atrial fibrillation and during automatic mode switch.

13. The method of claim 1 wherein deriving A-wave parameters from the atrial cardiogenic impedance values includes:
    generating an A-wave impedance template representative of active filling of the ventricles based on atrial cardiogenic impedance values measured during an initial period of non-demand pacing;
    measuring additional values representative of atrial impedance during a subsequent cardiac cycle; and determining a convolution of the A-wave impedance template with the additional atrial impedance values to derive A-wave parameters representative of active filling contributions to diastolic function within the subsequent cardiac cycle.

14. The method of claim 13 wherein the A-wave parameters representative of active filling contributions to diastolic function include a parameter representative of the timing of the A-wave.

15. The method of claim 14 wherein the timing of the A-wave of the subsequent cardiac cycle is determined based on a time shift resulting in a greatest correlation coefficient between the A-wave impedance template and the atrial impedance values of the subsequent cardiac cycle.

16. The method of claim 13 wherein the A-wave parameters include parameters representative of an amount of blood received by the ventricles during the particular cardiac cycle due to active filling.

17. The method of claim 16 wherein the parameters representative of the amount of blood received by the ventricles during active filling are determined based on a peak metric value of the greatest correlation coefficient between the A-wave impedance template and the additional atrial impedance values of the subsequent cardiac cycle.

18. The method of claim 16 wherein the parameters representative of the amount of blood received by the ventricles during active filling are determined based on a metric value obtained by calculating an integral of the atrial impedance values of the subsequent cardiac cycle for samples where a correlation coefficient between the A-wave impedance template and the atrial impedance values of the subsequent cardiac cycle exceeds a predetermined threshold.

19. The method of claim 13 wherein generating the A-wave impedance template includes:
 measuring values representative of atrial cardiogenic impedance during a period of non-demand pacing comprising a plurality of cardiac cycles;
 detecting atrial activation events within the cardiac cycles;
 aligning the measured atrial cardiogenic impedance values to the detected atrial activation events of corresponding cardiac cycles such that any corresponding ventricular activation events are approximately uniformly distributed so the contribution from ventricular activation and relaxation sums to a substantially negligible level;
 ensemble averaging the aligned atrial cardiogenic impedance values;
 identifying a segment of increasing impedance within the ensemble averaged atrial cardiogenic impedance values following corresponding atrial activation events within the cardiac cycles; and
 storing the segment of increasing impedance as the A-wave template.

20. The method of claim 1 wherein assessing diastolic function includes tracking passive filling contributions to diastolic function based on the E-wave parameters.

21. The method of claim 1 wherein assessing diastolic function includes tracking active filling contributions to diastolic function based on the A-wave parameters.

22. The method of claim 1 wherein assessing diastolic function includes one or more of detecting and tracking cardiac disease.

23. The method of claim 1 wherein controlling at least one device function based on the assessment of diastolic function includes adjusting an AV pacing delay based on the assessment of diastolic function.

24. The method of claim 23 wherein adjusting the AV pacing delay is performed to avoid one or more of fusion of A-wave and E-wave and truncation of the A-wave.

25. The method of claim 23 wherein adjusting the AV pacing delay is performed to increase a sum of E-wave and A-wave contributions to diastolic function derived from the E-wave and A-wave parameters.

26. The method of claim 1 wherein deriving E-wave parameters from the ventricular cardiogenic impedance values includes intermittently varying AV pacing delays from a currently-programmed setting to a different setting for a selected number of beats and generating an E-wave impedance template representative of passive filling of the ventricles based on ventricular cardiogenic impedance values measured while the AV delays are varied.

* * * * *